United States Patent [19]

Goldstein et al.

[11] Patent Number: 5,591,588
[45] Date of Patent: Jan. 7, 1997

[54] METHOD FOR THE DIAGNOSIS OF DEPRESSION BASED ON MONITORING BLOOD LEVELS OF ARGININE VASOPRESSIN AND/OR THYMOPOIETIN

[75] Inventors: Gideon Goldstein, 30 Dorison Dr., Short Hills, N.J. 07078; Michael D. Culler, Easton, Pa.

[73] Assignee: Gideon Goldstein, Short Hills, N.J.

[21] Appl. No.: 309,420

[22] Filed: Sep. 20, 1994

[51] Int. Cl.$^6$ ..................................................... G01N 33/53
[52] U.S. Cl. .................. 435/7.1; 435/7.92; 435/961; 435/975; 436/174; 436/518; 436/524; 436/528; 436/811
[58] Field of Search ................... 435/7.92, 7.93, 435/7.94, 7.95, 7.1, 961, 962, 967, 975; 436/518, 86, 87, 174, 175, 176, 177, 804, 811

[56] References Cited

U.S. PATENT DOCUMENTS 4,124,700  11/1978  Goldstein .................................. 436/542

OTHER PUBLICATIONS

E. Zimmerman, "Oxytocin, Vasopressin, and Neurophysin", *Brain Peptides*, D. Kreiger et al, eds. John Wiley & Sons, New York, Ch. 25, pp. 598–611 (Oct. 31, 1983).
D. deGoeij et al, "Chronic Phychological Stress Enhances Vasopressin, but not Corticotropin–Releasing Factor, in the External Zone of the Median Eminence of Male Rats: Relationship to Suborinate Status", *Endocrinol.*, 131 (2);847–853 (1992).
F. Antoni, "Vasopressinergic Control of Pituitary Adrenocorticotropin Secretion Comes of Age", *Frontiers in Neuroendocrinol.*, 14(2):76–122 (Mar. 1993).
M. Hammer, "Radioimmunoassay of 8–Arginine–Vasopressin (Antidiuretic Hormone) in Human Plasma", *Scand. J. Clin. Lab. Invest.*, 38:707–716 (1978).
P. Soelberg Sorensen et al, "Cerebrospinal Fluid Vasopressin in Neurological and Psychiatric Disorders", *J. Neurol. Neurosurg. and Phsych.*, 48:50–57 (Jan. 1985).
A. Gjerris, "Do Concentrations of Neurotransmitters in Lumbar CSF Reflect Cerebral Dysfunction in Depression?", *Acta Psychiatr. Scand.*, 78(345):21–24 (1988).
A. Gjerris et al, "Cerebrospinal Fluid Vasopressin —Changes in Depression", *British J. Phsychiat.*, 147:696–701 (Dec. 1985).
P. Gold et al, "Neurohypophyseal Function in Affective Illness", *Psychopharmacol. Bull.*, 19(3):426–431 (1983).
S. Hou, "Syndrome of Inappropriate Antidiuretic Hormone Secretion", *The Neurohypophysis*, Ch. 9, pp. 165–189, S. Reichlin, ed., Plenum Press, New York (May 1984).
*Textbook of Endocrinology*, 7th ed., Wilson & Foster, eds., pp. 644–645 (1985).

G. Sunshine et al, "Thymopoietin Enhances the Allogeneic Response and Cyclic GMP Levels of Mouse Peripheral, Thymus–Derived Lympohocytes", *J. Immunol.*, 120:1594–1599 (May 1978).
G. Goldstein, "Isolation of Bovine Thymin: a Polypeptide Hormone of the Thymus", *Nature*, 247:11–14 (Jan. 1974).
D. Schlesinger and G. Goldstein, "The Amino Acid Sequence of Thymopoietin II", *Cell*, 5:361–365 (Aug. 1975).
G. Goldstein et al, "Thymopoietin and Myasthenia Gravis: Neostigmine–Responsive Neuromuscular Block Produced in Mice by a Synthetic Peptide Fragment of Thymopoietin", *Lancet*, 2:256–262 (Aug. 1975).
R. Brown et al, "Immunoreactive Thymopoietin in the Mouse Central Nervous System", *Brain Research*, 381:237–243 (Aug. 1986).
J. Twomey et al, "Bioassay Determinations of Thymopoietin and Thymic Hormone Levels in Human Plasma", *Proc. Natl. Acad. Sci. USA*, 74:2541–2545 (Jun. 1977).
V. Lewis et al, "Age, Thymic Involution, and Circulating Thymic Hormone Activity", *J. Clin. Endo. Metab.*, 47(1):145–150 (Jul. 1978).
J. Twomey et al, "An Inhibitor of Thymic Hormone Activity in Serum from Patients with Lymphoblastic Leukemia", *Am. J. Med.*, 68:377–380 (Mar. 1980).
G. Goldstein, "Radioimmunoassay for Thymopoietin", *J. Immunol.*, 117:690–692 (Aug. 1976).
P. Lisi et al, "Improved Radioimmunoassay Technique for Measuring Serum Thymopoietin", *Clin. Chim. ACTA*, 107:111–119 (Oct. 1980).
A. Fuccello et al, "Immunoassay for Bovine Serum Thymopoietin: Discrimination from Splenin by Monoclonal Antibodies", *Arch. Biochem. Biophys.*, 228:292–298 (Jan. 1984).
G. Goldstein and I. Mackay, "The Thymus and Experimental Pathology", *The Human Thymus*, Wm. Heineman Med. Books Ltd., London (1969).
G. Goldstein, "Thymitis and Myasthenia Gravis", *Lancet*, 2:1164–1167 (Nov. 1966).
P. Gold et al, "Vasopressin Function in Depression and Mania", *Psychopharmacol. Bull.*, 17(1):7–9 (Jan. 1981).
P. Gold et al, "Central Peptide Function in Affective Illness: Arginine Vasopressin as a Model System", *Adv. Biol. Psychiat.*, 7:42–70 (1981).
Hammer M., Scand J. Clin. Lab. Invest. 38:707–716 (1978).

*Primary Examiner*—Marian C. Knode
*Assistant Examiner*—Patricia A. Duffy
*Attorney, Agent, or Firm*—Howson and Howson

[57] ABSTRACT

The invention provides a novel means of diagnosing, or confirming a diagnosis of, affective disorders, such as depression, based on the blood levels of arginine vasopressin and thymopoietin, either alone or in combination.

8 Claims, 5 Drawing Sheets

|  |  | DEPRESSED | CONTROL |
|---|---|---|---|
| TP | ≥6.4 pg/mL | 16 | 4 |
|  | <6.4 | 5 | 17 |
|  | ALL | 21 | 21 |
|  |  | SENSITIVITY 16/21=76% | SPECIFICITY 17/21=81% |
| AVP | ≥3.6 pg/mL | 17 | 5 |
|  | <3.6 | 4 | 16 |
|  | ALL | 21 | 21 |
|  |  | SENSITIVITY 17/21=81% | SPECIFICITY 16/21=76% |
| TP,AVP COMBINED | LOGISTICS MODEL PROBABILITY | ≥.5 | 17 | 2 |
|  | <.5 | 4 | 19 |
|  | ALL | 21 | 21 |
|  |  | SENSITIVITY 17/21=81% | SPECIFICITY 19/21=90% |

FIG. 5

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2490 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 205..2286

( x i ) SEQUENCE DESCRIPTION: SEQ ID NO:1:

```
GTTCGTAGTT  CGGCTCTGGG  GTCTTTTGTG  TCCGGGTCTG  GCTTGGCTTT  GTGTCCGCGA                60

GTTTTTGTTC  CGCTCCGCAG  CGCTCTTCCC  GGGCAGGAGC  CGTGAGGCTC  GGAGGCGGCA               120

GCGCGGTCCC  CGGCCAGGAG  CAAGCGCGCC  GGCGTGAGCG  GCGGCGGCAA  AGGCTGTGGG               180

GAGGGGGCTT  CGCAGATCCC  CGAG ATG CCG GAG TTC CTG GAA GAC CCC TCG                    231
                              Met Pro Glu Phe Leu Glu Asp Pro Ser
                               1               5

GTC CTG ACA AAA GAC AAG TTG AAG AGT GAG TTG GTC GCC AAC AAT GTG                     279
Val Leu Thr Lys Asp Lys Leu Lys Ser Glu Leu Val Ala Asn Asn Val
 10              15                  20                  25

ACG CTG CCG GCC GGG GAG CAG CGC AAA GAC GTG TAC GTC CAG CTC TAC                     327
Thr Leu Pro Ala Gly Glu Gln Arg Lys Asp Val Tyr Val Gln Leu Tyr
                 30                  35                  40

CTG CAG CAC CTC ACG GCT CGC AAC CGG CCG CCG CTC CCC GCC GGC ACC                     375
```

-continued

```
                Leu Gln His Leu Thr Ala Arg Asn Arg Pro Pro Leu Pro Ala Gly Thr
                             45                      50                  55

AAC AGC AAG GGG CCC CCG GAC TTC TCC AGT GAC GAA GAG CGC GAG CCC           423
Asn Ser Lys Gly Pro Pro Asp Phe Ser Ser Asp Glu Glu Arg Glu Pro
            60                      65                  70

ACC CCG GTC CTC GGC TCT GGG GCC GCC GCC GCG GGC CGG AGC CGA GCA           471
Thr Pro Val Leu Gly Ser Gly Ala Ala Ala Ala Gly Arg Ser Arg Ala
        75                      80                      85

GCC GTC GGC AGG AAA GCC ACA AAA AAA ACT GAT AAA CCC AGA CAA GAA           519
Ala Val Gly Arg Lys Ala Thr Lys Lys Thr Asp Lys Pro Arg Gln Glu
 90                      95                     100                 105

GAT AAA GAT GAT CTA GAT GTA ACA GAG CTC ACT AAT GAA GAT CTT TTG           567
Asp Lys Asp Asp Leu Asp Val Thr Glu Leu Thr Asn Glu Asp Leu Leu
                    110                     115                 120

GAT CAG CTT GTG AAA TAC GGA GTG AAT CCT GGT CCT ATT GTG GGA ACA           615
Asp Gln Leu Val Lys Tyr Gly Val Asn Pro Gly Pro Ile Val Gly Thr
            125                     130                 135

ACC AGG AAG CTA TAT GAG AAA AAG CTT TTG AAA CTG AGG GAA CAA GGA           663
Thr Arg Lys Leu Tyr Glu Lys Lys Leu Leu Lys Leu Arg Glu Gln Gly
        140                     145                 150

ACA GAA TCA AGA TCT TCT ACT CCT CTG CCA ACA ATT TCT TCT TCA GCA           711
Thr Glu Ser Arg Ser Ser Thr Pro Leu Pro Thr Ile Ser Ser Ser Ala
155                     160                     165

GAA AAT ACA AGG CAG AAT GGA AGT AAT GAT TCT GAC AGA TAC AGT GAC           759
Glu Asn Thr Arg Gln Asn Gly Ser Asn Asp Ser Asp Arg Tyr Ser Asp
170                     175                 180                     185

AAT GAA GAA GGA AAG AAG AAA GAA CAC AAG AAA GTG AAG TCC ACT AGG           807
Asn Glu Glu Gly Lys Lys Lys Glu His Lys Lys Val Lys Ser Thr Arg
                    190                 195                 200

GAT ATT GTT CCT TTT TCT GAA CTT GGA ACT ACT CCC TCT GGT GGT GGA           855
Asp Ile Val Pro Phe Ser Glu Leu Gly Thr Thr Pro Ser Gly Gly Gly
                205                     210                 215

TTT TTT CAG GGT ATT TCT TTT CCT GAA ATC TCC ACC CGT CCT CCT TTG           903
Phe Phe Gln Gly Ile Ser Phe Pro Glu Ile Ser Thr Arg Pro Pro Leu
            220                     225                 230

GGC AGT ACC GAA CTA CAG GCA GCT AAG AAA GTA CAT ACT TCT AAG GGA           951
Gly Ser Thr Glu Leu Gln Ala Ala Lys Lys Val His Thr Ser Lys Gly
235                     240                     245

GAC CTA CCT AGG GAG CCT CTT GTT GCC ACA AAC TTG CCT GGC AGG GGA           999
Asp Leu Pro Arg Glu Pro Leu Val Ala Thr Asn Leu Pro Gly Arg Gly
250                     255                 260                     265

CAG TTG CAG AAG TTA GCC TCT GAA AGG AAT TTG TTT ATT TCA TGC AAG          1047
Gln Leu Gln Lys Leu Ala Ser Glu Arg Asn Leu Phe Ile Ser Cys Lys
                270                     275                 280

TCT AGC CAT GAT AGG TGT TTA GAG AAA AGT TCT TCG TCA TCT TCT CAG          1095
Ser Ser His Asp Arg Cys Leu Glu Lys Ser Ser Ser Ser Ser Ser Gln
            285                     290                 295

CCT GAA CAC AGT GCC ATG TTG GTC TCT ACT GCA GCT TCT CCT TCA CTG          1143
Pro Glu His Ser Ala Met Leu Val Ser Thr Ala Ala Ser Pro Ser Leu
        300                     305                 310

ATT AAA GAA ACC ACC ACT GGT TAC TAT AAA GAC ATA GTA GAA AAT ATT          1191
Ile Lys Glu Thr Thr Thr Gly Tyr Tyr Lys Asp Ile Val Glu Asn Ile
315                     320                 325

TGC GGT AGA GAG AAA AGT GGA ATT CAA CCA TTA TGT CCT GAG AGG TCC          1239
Cys Gly Arg Glu Lys Ser Gly Ile Gln Pro Leu Cys Pro Glu Arg Ser
330                     335                 340                     345

CAT ATT TCA GAT CAA TCG CCT CTC TCC AGT AAA AGG AAA GCA CTA GAA          1287
His Ile Ser Asp Gln Ser Pro Leu Ser Ser Lys Arg Lys Ala Leu Glu
                350                     355                 360

GAG TCT GAG AGC TCA CAA CTA ATT TCT CCG CCA CTT GCC CAG GCA ATC          1335
```

|         |         |         |         |         |         |         |         |         |         |         |         |         |         |         |         |      |
|---------|---------|---------|---------|---------|---------|---------|---------|---------|---------|---------|---------|---------|---------|---------|---------|------|
| Glu | Ser | Glu | Ser | Ser | Gln | Leu | Ile | Ser | Pro | Pro | Leu | Ala | Gln | Ala | Ile | |
|     |     | 365 |     |     |     |     | 370 |     |     |     |     |     | 375 |     |     | |

| AGA | GAT | TAT | GTC | AAT | TCT | CTG | TTG | GTC | CAG | GGT | GGG | GTA | GGT | AGT | TTG | 1383 |
| Arg | Asp | Tyr | Val | Asn | Ser | Leu | Leu | Val | Gln | Gly | Gly | Val | Gly | Ser | Leu | |
|     |     | 380 |     |     |     |     | 385 |     |     |     |     | 390 |     |     |     | |

| CCT | GGA | ACT | TCT | AAC | TCT | ATG | CCC | CCA | CTG | GAT | GTA | GAA | AAC | ATA | CAG | 1431 |
| Pro | Gly | Thr | Ser | Asn | Ser | Met | Pro | Pro | Leu | Asp | Val | Glu | Asn | Ile | Gln | |
| 395 |     |     |     |     |     | 400 |     |     |     |     | 405 |     |     |     |     | |

| AAG | AGA | ATT | GAT | CAG | TCT | AAG | TTT | CAA | GAA | ACT | GAA | TTC | CTG | TCT | CCT | 1479 |
| Lys | Arg | Ile | Asp | Gln | Ser | Lys | Phe | Gln | Glu | Thr | Glu | Phe | Leu | Ser | Pro | |
| 410 |     |     |     |     | 415 |     |     |     |     | 420 |     |     |     |     | 425 | |

| CCA | AGA | AAA | GTC | CCT | AGA | CTG | AGT | GAG | AAG | TCA | GTG | GAG | GAA | AGG | GAT | 1527 |
| Pro | Arg | Lys | Val | Pro | Arg | Leu | Ser | Glu | Lys | Ser | Val | Glu | Glu | Arg | Asp | |
|     |     |     |     | 430 |     |     |     |     | 435 |     |     |     |     | 440 |     | |

| TCA | GGT | TCC | TTT | GTG | GCA | TTT | CAG | AAC | ATA | CCT | GGA | TCC | GAA | CTG | ATG | 1575 |
| Ser | Gly | Ser | Phe | Val | Ala | Phe | Gln | Asn | Ile | Pro | Gly | Ser | Glu | Leu | Met | |
|     |     |     | 445 |     |     |     |     | 450 |     |     |     |     | 455 |     |     | |

| TCT | TCT | TTT | GCC | AAA | ACT | GTT | GTC | TCT | CAT | TCA | CTC | ACT | ACC | TTA | GGT | 1623 |
| Ser | Ser | Phe | Ala | Lys | Thr | Val | Val | Ser | His | Ser | Leu | Thr | Thr | Leu | Gly | |
|     |     | 460 |     |     |     |     | 465 |     |     |     |     | 470 |     |     |     | |

| CTA | GAA | GTG | GCT | AAG | CAA | TCA | CAG | CAT | GAT | AAA | ATA | GAT | GCC | TCA | GAA | 1671 |
| Leu | Glu | Val | Ala | Lys | Gln | Ser | Gln | His | Asp | Lys | Ile | Asp | Ala | Ser | Glu | |
|     | 475 |     |     |     |     | 480 |     |     |     |     | 485 |     |     |     |     | |

| CTA | TCT | TTT | CCC | TTC | CAT | GAA | TCT | ATT | TTA | AAA | GTA | ATT | GAA | GAA | GAA | 1719 |
| Leu | Ser | Phe | Pro | Phe | His | Glu | Ser | Ile | Leu | Lys | Val | Ile | Glu | Glu | Glu | |
| 490 |     |     |     |     | 495 |     |     |     |     | 500 |     |     |     |     | 505 | |

| TGG | CAG | CAA | GTT | GAC | AGG | CAG | CTG | CCT | TCA | CTG | GCA | TGC | AAA | TAT | CCA | 1767 |
| Trp | Gln | Gln | Val | Asp | Arg | Gln | Leu | Pro | Ser | Leu | Ala | Cys | Lys | Tyr | Pro | |
|     |     |     |     | 510 |     |     |     |     | 515 |     |     |     |     | 520 |     | |

| GTT | TCT | TCC | AGG | GAG | GCA | ACA | CAG | ATA | TTA | TCA | GTT | CCA | AAA | GTA | GAT | 1815 |
| Val | Ser | Ser | Arg | Glu | Ala | Thr | Gln | Ile | Leu | Ser | Val | Pro | Lys | Val | Asp | |
|     |     |     | 525 |     |     |     |     | 530 |     |     |     |     | 535 |     |     | |

| GAT | GAA | ATC | CTA | GGG | TTT | ATT | TCT | GAA | GCC | ACT | CCA | CTA | GGA | GGT | ATT | 1863 |
| Asp | Glu | Ile | Leu | Gly | Phe | Ile | Ser | Glu | Ala | Thr | Pro | Leu | Gly | Gly | Ile | |
|     |     | 540 |     |     |     |     | 545 |     |     |     |     | 550 |     |     |     | |

| CAA | GCA | GCC | TCC | ACT | GAG | TCT | TGC | AAT | CAG | CAG | TTG | GAC | TTA | GCA | CTC | 1911 |
| Gln | Ala | Ala | Ser | Thr | Glu | Ser | Cys | Asn | Gln | Gln | Leu | Asp | Leu | Ala | Leu | |
| 555 |     |     |     |     | 560 |     |     |     |     | 565 |     |     |     |     |     | |

| TGT | AGA | GCA | TAT | GAA | GCT | GCA | GCA | TCA | GCA | TTG | CAG | ATT | GCA | ACT | CAC | 1959 |
| Cys | Arg | Ala | Tyr | Glu | Ala | Ala | Ala | Ser | Ala | Leu | Gln | Ile | Ala | Thr | His | |
| 570 |     |     |     | 575 |     |     |     |     | 580 |     |     |     |     | 585 |     | |

| ACT | GCC | TTT | GTA | GCT | AAG | GCT | ATG | CAG | GCA | GAC | ATT | AGT | CAA | GCT | GCA | 2007 |
| Thr | Ala | Phe | Val | Ala | Lys | Ala | Met | Gln | Ala | Asp | Ile | Ser | Gln | Ala | Ala | |
|     |     |     |     | 590 |     |     |     |     | 595 |     |     |     |     | 600 |     | |

| CAG | ATT | CTT | AGC | TCA | GAT | CCT | AGT | CGT | ACC | CAC | CAA | GCG | CTT | GGG | ATT | 2055 |
| Gln | Ile | Leu | Ser | Ser | Asp | Pro | Ser | Arg | Thr | His | Gln | Ala | Leu | Gly | Ile | |
|     |     |     | 605 |     |     |     |     | 610 |     |     |     |     | 615 |     |     | |

| CTG | AGC | AAA | ACA | TAT | GAT | GCA | GCC | TCA | TAT | ATT | TGT | GAA | GCT | GCA | TTT | 2103 |
| Leu | Ser | Lys | Thr | Tyr | Asp | Ala | Ala | Ser | Tyr | Ile | Cys | Glu | Ala | Ala | Phe | |
|     | 620 |     |     |     |     | 625 |     |     |     |     | 630 |     |     |     |     | |

| GAT | GAA | GTG | AAG | ATG | GCT | GCC | CAT | ACC | ATG | GGA | AAT | GCC | ACT | GTA | GGT | 2151 |
| Asp | Glu | Val | Lys | Met | Ala | Ala | His | Thr | Met | Gly | Asn | Ala | Thr | Val | Gly | |
|     | 635 |     |     |     |     | 640 |     |     |     |     | 645 |     |     |     |     | |

| CGT | CGA | TAC | CTC | TGG | CTG | AAG | GAT | TGC | AAA | ATT | AAT | TTA | GCT | TCT | AAG | 2199 |
| Arg | Arg | Tyr | Leu | Trp | Leu | Lys | Asp | Cys | Lys | Ile | Asn | Leu | Ala | Ser | Lys | |
| 650 |     |     |     | 655 |     |     |     |     | 660 |     |     |     |     | 665 |     | |

| AAT | AAG | CTG | GCT | TCC | ACT | CCC | TTT | AAA | GGT | GGA | ACA | TTA | TTT | GGA | GGA | 2247 |
| Asn | Lys | Leu | Ala | Ser | Thr | Pro | Phe | Lys | Gly | Gly | Thr | Leu | Phe | Gly | Gly | |
|     |     |     |     | 670 |     |     |     |     | 675 |     |     |     |     | 680 |     | |

| GAA | GTA | TGC | AAA | GTA | ATT | AAA | AAG | CGT | GGA | AAT | AAA | CAC | TAGTAAAATT | | | 2296 |

|   |   |   |   |   |   |   |   |   |   |   |   |   |   |   |
|---|---|---|---|---|---|---|---|---|---|---|---|---|---|---|
| Glu | Val | Cys | Lys 685 | Val | Ile | Lys | Lys | Arg 690 | Gly | Asn | Lys | His |   |   |

```
AAGGACAAAA AGACATCTAT CTTATCTTTC AGGTACTTTA TGCCAACATT TTCTTTTCTG   2356

TTAAGGTTGT TTTAGTTTCC AGATAGGGCT AATTACAAAA TGTTAAGCTT CTACCCATCA   2416

AATTACAGTA TAAAAGTAAT TGCCTGTGTA GAACTACTTG TCTTTTCTAA AGATTTGCGT   2476

AGATAGGAAG CCTG                                                     2490
```

( 2 ) INFORMATION FOR SEQ ID NO:2:

( i ) SEQUENCE CHARACTERISTICS:
            ( A ) LENGTH: 694 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

| Met 1 | Pro | Glu | Phe | Leu 5 | Glu | Asp | Pro | Ser | Val 10 | Leu | Thr | Lys | Asp | Leu 15 |
|---|---|---|---|---|---|---|---|---|---|---|---|---|---|---|
| Lys | Ser | Glu | Leu 20 | Val | Ala | Asn | Asn | Val 25 | Thr | Leu | Pro | Ala | Gly 30 | Glu | Gln |
| Arg | Lys | Asp 35 | Val | Tyr | Val | Gln | Leu 40 | Tyr | Leu | Gln | His | Leu 45 | Thr | Ala | Arg |
| Asn | Arg 50 | Pro | Pro | Leu | Pro | Ala 55 | Gly | Thr | Asn | Ser | Lys 60 | Gly | Pro | Pro | Asp |
| Phe 65 | Ser | Ser | Asp | Glu | Glu 70 | Arg | Glu | Pro | Thr | Pro 75 | Val | Leu | Gly | Ser | Gly 80 |
| Ala | Ala | Ala | Ala | Gly 85 | Arg | Ser | Arg | Ala | Ala 90 | Val | Gly | Arg | Lys | Ala 95 | Thr |
| Lys | Lys | Thr | Asp 100 | Lys | Pro | Arg | Gln | Glu 105 | Asp | Lys | Asp | Asp | Leu 110 | Asp | Val |
| Thr | Glu | Leu 115 | Thr | Asn | Glu | Asp | Leu 120 | Leu | Asp | Gln | Leu | Val 125 | Lys | Tyr | Gly |
| Val | Asn 130 | Pro | Gly | Pro | Ile | Val 135 | Gly | Thr | Thr | Arg | Lys 140 | Leu | Tyr | Glu | Lys |
| Lys 145 | Leu | Leu | Lys | Leu | Arg 150 | Glu | Gln | Gly | Thr | Glu 155 | Ser | Arg | Ser | Ser | Thr 160 |
| Pro | Leu | Pro | Thr | Ile 165 | Ser | Ser | Ser | Ala | Glu 170 | Asn | Thr | Arg | Gln | Asn 175 | Gly |
| Ser | Asn | Asp | Ser 180 | Asp | Arg | Tyr | Ser | Asp 185 | Asn | Glu | Glu | Gly | Lys 190 | Lys | Lys |
| Glu | His | Lys 195 | Lys | Val | Lys | Ser | Thr 200 | Arg | Asp | Ile | Val | Pro 205 | Phe | Ser | Glu |
| Leu | Gly 210 | Thr | Thr | Pro | Ser | Gly 215 | Gly | Gly | Phe | Phe | Gln 220 | Gly | Ile | Ser | Phe |
| Pro 225 | Glu | Ile | Ser | Thr | Arg 230 | Pro | Pro | Leu | Gly | Ser 235 | Thr | Glu | Leu | Gln | Ala 240 |
| Ala | Lys | Lys | Val | His 245 | Thr | Ser | Lys | Gly | Asp 250 | Leu | Pro | Arg | Glu | Pro 255 | Leu |
| Val | Ala | Thr | Asn 260 | Leu | Pro | Gly | Arg | Gly 265 | Gln | Leu | Gln | Lys | Leu 270 | Ala | Ser |
| Glu | Arg | Asn 275 | Leu | Phe | Ile | Ser | Cys 280 | Lys | Ser | Ser | His | Asp 285 | Arg | Cys | Leu |
| Glu | Lys 290 | Ser | Ser | Ser | Ser | Ser 295 | Ser | Gln | Pro | Glu | His 300 | Ser | Ala | Met | Leu |

| Val | Ser | Thr | Ala | Ala | Ser | Pro | Ser | Leu | Ile | Lys | Glu | Thr | Thr | Thr | Gly |
| 305 | | | | 310 | | | | | 315 | | | | | | 320 |

| Tyr | Tyr | Lys | Asp | Ile | Val | Glu | Asn | Ile | Cys | Gly | Arg | Glu | Lys | Ser | Gly |
| | | | 325 | | | | | 330 | | | | | 335 | | |

| Ile | Gln | Pro | Leu | Cys | Pro | Glu | Arg | Ser | His | Ile | Ser | Asp | Gln | Ser | Pro |
| | | | 340 | | | | | 345 | | | | | 350 | | |

| Leu | Ser | Ser | Lys | Arg | Lys | Ala | Leu | Glu | Glu | Ser | Glu | Ser | Ser | Gln | Leu |
| | | 355 | | | | | 360 | | | | | 365 | | | |

| Ile | Ser | Pro | Pro | Leu | Ala | Gln | Ala | Ile | Arg | Asp | Tyr | Val | Asn | Ser | Leu |
| | 370 | | | | | 375 | | | | | 380 | | | | |

| Leu | Val | Gln | Gly | Gly | Val | Gly | Ser | Leu | Pro | Gly | Thr | Ser | Asn | Ser | Met |
| 385 | | | | | 390 | | | | | 395 | | | | | 400 |

| Pro | Pro | Leu | Asp | Val | Glu | Asn | Ile | Gln | Lys | Arg | Ile | Asp | Gln | Ser | Lys |
| | | | | 405 | | | | | 410 | | | | | 415 | |

| Phe | Gln | Glu | Thr | Glu | Phe | Leu | Ser | Pro | Pro | Arg | Lys | Val | Pro | Arg | Leu |
| | | | 420 | | | | | 425 | | | | | 430 | | |

| Ser | Glu | Lys | Ser | Val | Glu | Glu | Arg | Asp | Ser | Gly | Ser | Phe | Val | Ala | Phe |
| | | 435 | | | | | 440 | | | | | 445 | | | |

| Gln | Asn | Ile | Pro | Gly | Ser | Glu | Leu | Met | Ser | Ser | Phe | Ala | Lys | Thr | Val |
| | 450 | | | | | 455 | | | | | 460 | | | | |

| Val | Ser | His | Ser | Leu | Thr | Thr | Leu | Gly | Leu | Glu | Val | Ala | Lys | Gln | Ser |
| 465 | | | | | 470 | | | | | 475 | | | | | 480 |

| Gln | His | Asp | Lys | Ile | Asp | Ala | Ser | Glu | Leu | Ser | Phe | Pro | Phe | His | Glu |
| | | | | 485 | | | | | 490 | | | | | 495 | |

| Ser | Ile | Leu | Lys | Val | Ile | Glu | Glu | Trp | Gln | Gln | Val | Asp | Arg | Gln |
| | | | 500 | | | | | 505 | | | | | 510 | | |

| Leu | Pro | Ser | Leu | Ala | Cys | Lys | Tyr | Pro | Val | Ser | Ser | Arg | Glu | Ala | Thr |
| | | 515 | | | | | 520 | | | | | 525 | | | |

| Gln | Ile | Leu | Ser | Val | Pro | Lys | Val | Asp | Asp | Glu | Ile | Leu | Gly | Phe | Ile |
| | 530 | | | | | 535 | | | | | 540 | | | | |

| Ser | Glu | Ala | Thr | Pro | Leu | Gly | Gly | Ile | Gln | Ala | Ala | Ser | Thr | Glu | Ser |
| 545 | | | | | 550 | | | | | 555 | | | | | 560 |

| Cys | Asn | Gln | Gln | Leu | Asp | Leu | Ala | Leu | Cys | Arg | Ala | Tyr | Glu | Ala | Ala |
| | | | | 565 | | | | | 570 | | | | | 575 | |

| Ala | Ser | Ala | Leu | Gln | Ile | Ala | Thr | His | Thr | Ala | Phe | Val | Ala | Lys | Ala |
| | | | 580 | | | | | 585 | | | | | 590 | | |

| Met | Gln | Ala | Asp | Ile | Ser | Gln | Ala | Ala | Gln | Ile | Leu | Ser | Ser | Asp | Pro |
| | | 595 | | | | | 600 | | | | | 605 | | | |

| Ser | Arg | Thr | His | Gln | Ala | Leu | Gly | Ile | Leu | Ser | Lys | Thr | Tyr | Asp | Ala |
| | 610 | | | | | 615 | | | | | 620 | | | | |

| Ala | Ser | Tyr | Ile | Cys | Glu | Ala | Ala | Phe | Asp | Glu | Val | Lys | Met | Ala | Ala |
| 625 | | | | | 630 | | | | | 635 | | | | | 640 |

| His | Thr | Met | Gly | Asn | Ala | Thr | Val | Gly | Arg | Arg | Tyr | Leu | Trp | Leu | Lys |
| | | | | 645 | | | | | 650 | | | | | 655 | |

| Asp | Cys | Lys | Ile | Asn | Leu | Ala | Ser | Lys | Asn | Lys | Leu | Ala | Ser | Thr | Pro |
| | | | 660 | | | | | 665 | | | | | 670 | | |

| Phe | Lys | Gly | Gly | Thr | Leu | Phe | Gly | Gly | Glu | Val | Cys | Lys | Val | Ile | Lys |
| | | 675 | | | | | 680 | | | | | 685 | | | |

| Lys | Arg | Gly | Asn | Lys | His |
| | 690 | | | | |

( 2 ) INFORMATION FOR SEQ ID NO:3:

( i ) SEQUENCE CHARACTERISTICS:
        ( A ) LENGTH: 1743 base pairs ( B ) TYPE: nucleic acid
( C ) STRANDEDNESS: double
( D ) TOPOLOGY: unknown ( i i ) MOLECULE TYPE: cDNA ( i x ) FEATURE:
( A ) NAME/KEY: CDS
( B ) LOCATION: 238..1599

( x i ) SEQUENCE DESCRIPTION: SEQ ID NO:3:

| | | | | | | |
|---|---|---|---|---|---|---|
| GGTTGGTGCG | AGCTTCCAGC | TTGGCCGCAG | TTGGTTCGTA | GTTCGGCTCT | GGGGTCTTTT | 60 |
| GTGTCCGGGT | CTGGCTTGGC | TTTGTGTCCG | CGAGTTTTTG | TTCCGCTCCG | CAGCGCTCTT | 120 |
| CCCGGGCAGG | AGCCGTGAGG | CTCGGAGGCG | GCAGCGCGGT | CCCCGGCCAG | GAGCAAGCGC | 180 |
| GCCGGCGTGA | GCGGCGGCGG | CAAAGGCTGT | GGGGAGGGGG | CTTCGCAGAT | CCCCGAG | 237 |

| ATG | CCG | GAG | TTC | CTG | GAA | GAC | CCC | TCG | GTC | CTG | ACA | AAA | GAC | AAG | TTG | 285 |
|---|---|---|---|---|---|---|---|---|---|---|---|---|---|---|---|---|
| Met | Pro | Glu | Phe | Leu | Glu | Asp | Pro | Ser | Val | Leu | Thr | Lys | Asp | Lys | Leu | |
| 1 | | | | 5 | | | | | 10 | | | | | 15 | | |

| AAG | AGT | GAG | TTG | GTC | GCC | AAC | AAT | GTG | ACG | CTG | CCG | GCC | GGG | GAG | CAG | 333 |
|---|---|---|---|---|---|---|---|---|---|---|---|---|---|---|---|---|
| Lys | Ser | Glu | Leu | Val | Ala | Asn | Asn | Val | Thr | Leu | Pro | Ala | Gly | Glu | Gln | |
| | | | 20 | | | | | 25 | | | | | 30 | | | |

| CGC | AAA | GAC | GTG | TAC | GTC | CAG | CTC | TAC | CTG | CAG | CAC | CTC | ACG | GCT | CGC | 381 |
|---|---|---|---|---|---|---|---|---|---|---|---|---|---|---|---|---|
| Arg | Lys | Asp | Val | Tyr | Val | Gln | Leu | Tyr | Leu | Gln | His | Leu | Thr | Ala | Arg | |
| | | 35 | | | | | 40 | | | | | 45 | | | | |

| AAC | CGG | CCG | CCG | CTC | CCC | GCC | GGC | ACC | AAC | AGC | AAG | GGG | CCC | CCG | GAC | 429 |
|---|---|---|---|---|---|---|---|---|---|---|---|---|---|---|---|---|
| Asn | Arg | Pro | Pro | Leu | Pro | Ala | Gly | Thr | Asn | Ser | Lys | Gly | Pro | Pro | Asp | |
| | 50 | | | | | 55 | | | | | 60 | | | | | |

| TTC | TCC | AGT | GAC | GAA | GAG | CGC | GAG | CCC | ACC | CCG | GTC | CTC | GGC | TCT | GGG | 477 |
|---|---|---|---|---|---|---|---|---|---|---|---|---|---|---|---|---|
| Phe | Ser | Ser | Asp | Glu | Glu | Arg | Glu | Pro | Thr | Pro | Val | Leu | Gly | Ser | Gly | |
| 65 | | | | 70 | | | | | 75 | | | | | 80 | | |

| GCC | GCC | GCC | GCG | GGC | CGG | AGC | CGA | GCA | GCC | GTC | GGC | AGG | AAA | GCC | ACA | 525 |
|---|---|---|---|---|---|---|---|---|---|---|---|---|---|---|---|---|
| Ala | Ala | Ala | Ala | Gly | Arg | Ser | Arg | Ala | Ala | Val | Gly | Arg | Lys | Ala | Thr | |
| | | | 85 | | | | | 90 | | | | | 95 | | | |

| AAA | AAA | ACT | GAT | AAA | CCC | AGA | CAA | GAA | GAT | AAA | GAT | GAT | CTA | GAT | GTA | 573 |
|---|---|---|---|---|---|---|---|---|---|---|---|---|---|---|---|---|
| Lys | Lys | Thr | Asp | Lys | Pro | Arg | Gln | Glu | Asp | Lys | Asp | Asp | Leu | Asp | Val | |
| | | | 100 | | | | | 105 | | | | | 110 | | | |

| ACA | GAG | CTC | ACT | AAT | GAA | GAT | CTT | TTG | GAT | CAG | CTT | GTG | AAA | TAC | GGA | 621 |
|---|---|---|---|---|---|---|---|---|---|---|---|---|---|---|---|---|
| Thr | Glu | Leu | Thr | Asn | Glu | Asp | Leu | Leu | Asp | Gln | Leu | Val | Lys | Tyr | Gly | |
| | | 115 | | | | | 120 | | | | | 125 | | | | |

| GTG | AAT | CCT | GGT | CCT | ATT | GTG | GGA | ACA | ACC | AGG | AAG | CTA | TAT | GAG | AAA | 669 |
|---|---|---|---|---|---|---|---|---|---|---|---|---|---|---|---|---|
| Val | Asn | Pro | Gly | Pro | Ile | Val | Gly | Thr | Thr | Arg | Lys | Leu | Tyr | Glu | Lys | |
| | 130 | | | | | 135 | | | | | 140 | | | | | |

| AAG | CTT | TTG | AAA | CTG | AGG | GAA | CAA | GGA | ACA | GAA | TCA | AGA | TCT | TCT | ACT | 717 |
|---|---|---|---|---|---|---|---|---|---|---|---|---|---|---|---|---|
| Lys | Leu | Leu | Lys | Leu | Arg | Glu | Gln | Gly | Thr | Glu | Ser | Arg | Ser | Ser | Thr | |
| 145 | | | | | 150 | | | | | 155 | | | | | 160 | |

| CCT | CTG | CCA | ACA | ATT | TCT | TCT | TCA | GCA | GAA | AAT | ACA | AGG | CAG | AAT | GGA | 765 |
|---|---|---|---|---|---|---|---|---|---|---|---|---|---|---|---|---|
| Pro | Leu | Pro | Thr | Ile | Ser | Ser | Ser | Ala | Glu | Asn | Thr | Arg | Gln | Asn | Gly | |
| | | | | 165 | | | | | 170 | | | | | 175 | | |

| AGT | AAT | GAT | TCT | GAC | AGA | TAC | AGT | GAC | AAT | GAA | GAA | GAC | TCT | AAA | ATA | 813 |
|---|---|---|---|---|---|---|---|---|---|---|---|---|---|---|---|---|
| Ser | Asn | Asp | Ser | Asp | Arg | Tyr | Ser | Asp | Asn | Glu | Glu | Asp | Ser | Lys | Ile | |
| | | | 180 | | | | | 185 | | | | | 190 | | | |

| GAG | CTC | AAG | CTT | GAG | AAG | AGA | GAA | CCA | CTA | AAG | GGC | AGA | GCA | AAG | ACT | 861 |
|---|---|---|---|---|---|---|---|---|---|---|---|---|---|---|---|---|
| Glu | Leu | Lys | Leu | Glu | Lys | Arg | Glu | Pro | Leu | Lys | Gly | Arg | Ala | Lys | Thr | |
| | | 195 | | | | | 200 | | | | | 205 | | | | |

| CCA | GTA | ACA | CTC | AAG | CAA | AGA | AGA | GTT | GAG | CAC | AAT | CAG | AGC | TAT | TCT | 909 |
|---|---|---|---|---|---|---|---|---|---|---|---|---|---|---|---|---|
| Pro | Val | Thr | Leu | Lys | Gln | Arg | Arg | Val | Glu | His | Asn | Gln | Ser | Tyr | Ser | |
| | 210 | | | | | 215 | | | | | 220 | | | | | |

| CAA | GCT | GGA | ATA | ACT | GAG | ACT | GAA | TGG | ACA | AGT | GGA | TCT | TCA | AAA | GGC | 957 |
|---|---|---|---|---|---|---|---|---|---|---|---|---|---|---|---|---|
| Gln | Ala | Gly | Ile | Thr | Glu | Thr | Glu | Trp | Thr | Ser | Gly | Ser | Ser | Lys | Gly | |
| 225 | | | | | 230 | | | | | 235 | | | | | 240 | |

```
GGA CCT CTG CAG GCA TTA ACT AGG GAA TCT ACA AGA GGG TCA AGA AGA      1005
Gly Pro Leu Gln Ala Leu Thr Arg Glu Ser Thr Arg Gly Ser Arg Arg
            245                 250                 255

ACT CCA AGG AAA AGG GTG GAA ACT TCA GAA CAT TTT CGT ATA GAT GGT      1053
Thr Pro Arg Lys Arg Val Glu Thr Ser Glu His Phe Arg Ile Asp Gly
        260                 265                 270

CCA GTA ATT TCA GAG AGT ACT CCC ATA GCT GAA ACT ATA ATG GCT TCA      1101
Pro Val Ile Ser Glu Ser Thr Pro Ile Ala Glu Thr Ile Met Ala Ser
            275                 280                 285

AGC AAC GAA TCC TTA GTT GTC AAT AGG GTG ACT GGA AAT TTC AAG CAT      1149
Ser Asn Glu Ser Leu Val Val Asn Arg Val Thr Gly Asn Phe Lys His
        290                 295                 300

GCA TCT CCT ATT CTG CCA ATC ACT GAA TTC TCA GAC ATA CCC AGA AGA      1197
Ala Ser Pro Ile Leu Pro Ile Thr Glu Phe Ser Asp Ile Pro Arg Arg
305                 310                 315                 320

GCA CCA AAG AAA CCA TTG ACA AGA GCT GAA GTG GGA GAA AAA ACA GAG      1245
Ala Pro Lys Lys Pro Leu Thr Arg Ala Glu Val Gly Glu Lys Thr Glu
        325                 330                 335

GAA AGA AGA GTA GAA AGG GAT ATT CTT AAG GAA ATG TTC CCC TAT GAA      1293
Glu Arg Arg Val Glu Arg Asp Ile Leu Lys Glu Met Phe Pro Tyr Glu
            340                 345                 350

GCA TCT ACA CCA ACA GGA ATT AGT GCT AGT TGC CGC AGA CCA ATC AAA      1341
Ala Ser Thr Pro Thr Gly Ile Ser Ala Ser Cys Arg Arg Pro Ile Lys
        355                 360                 365

GGG GCT GCA GGC CGG CCA TTA GAA CTC AGT GAT TTC AGG ATG GAG GAG      1389
Gly Ala Ala Gly Arg Pro Leu Glu Leu Ser Asp Phe Arg Met Glu Glu
370                 375                 380

TCT TTT TCA TCT AAA TAT GTT CCT AAG TAT GTT CCC TTG GCA GAT GTC      1437
Ser Phe Ser Ser Lys Tyr Val Pro Lys Tyr Val Pro Leu Ala Asp Val
385                 390                 395                 400

AAG TCA GAA AAG ACA AAA AAG GGA CGC TCC ATT CCC GTA TGG ATA AAA      1485
Lys Ser Glu Lys Thr Lys Lys Gly Arg Ser Ile Pro Val Trp Ile Lys
                405                 410                 415

ATT TTG CTG TTT GTT GTT GTG GCA GTT TTT TTG TTT TTG GTC TAT CAA      1533
Ile Leu Leu Phe Val Val Val Ala Val Phe Leu Phe Leu Val Tyr Gln
            420                 425                 430

GCT ATG GAA ACC AAC CAA GTA AAT CCC TTC TCT AAT TTT CTT CAT GTT      1581
Ala Met Glu Thr Asn Gln Val Asn Pro Phe Ser Asn Phe Leu His Val
        435                 440                 445

GAC CCT AGA AAA TCC AAC TGAATGGTAT CTCTTTGGCA CGTTCAACTT             1629
Asp Pro Arg Lys Ser Asn
450

GGTCTCCTAT TTTCAATAAC TGTTGAAAAA CATTTGTGTA CACTTGTTGA CTCCAAGAAC    1689

TAAAAATAAT GTGATTTCGC CTCAATAAAT GTAGTATTTC ATTGAAAAGC AAAC          1743
```

( 2 ) INFORMATION FOR SEQ ID NO:4:

( i ) SEQUENCE CHARACTERISTICS:
        ( A ) LENGTH: 454 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Pro Glu Phe Leu Glu Asp Pro Ser Val Leu Thr Lys Asp Lys Leu
 1               5                  10                  15

Lys Ser Glu Leu Val Ala Asn Asn Val Thr Leu Pro Ala Gly Glu Gln
            20                  25                  30

Arg Lys Asp Val Tyr Val Gln Leu Tyr Leu Gln His Leu Thr Ala Arg
        35                  40                  45
```

```
Asn  Arg  Pro  Pro  Leu  Pro  Ala  Gly  Thr  Asn  Ser  Lys  Gly  Pro  Pro  Asp
     50                  55                      60

Phe  Ser  Ser  Asp  Glu  Glu  Arg  Glu  Pro  Thr  Pro  Val  Leu  Gly  Ser  Gly
65                       70                  75                           80

Ala  Ala  Ala  Ala  Gly  Arg  Ser  Arg  Ala  Ala  Val  Gly  Arg  Lys  Ala  Thr
                    85                  90                      95

Lys  Lys  Thr  Asp  Lys  Pro  Arg  Gln  Glu  Asp  Lys  Asp  Asp  Leu  Asp  Val
               100                 105                     110

Thr  Glu  Leu  Thr  Asn  Glu  Asp  Leu  Leu  Asp  Gln  Leu  Val  Lys  Tyr  Gly
          115                      120                 125

Val  Asn  Pro  Gly  Pro  Ile  Val  Gly  Thr  Thr  Arg  Lys  Leu  Tyr  Glu  Lys
     130                 135                      140

Lys  Leu  Leu  Lys  Leu  Arg  Glu  Gln  Gly  Thr  Glu  Ser  Arg  Ser  Ser  Thr
145                      150                 155                          160

Pro  Leu  Pro  Thr  Ile  Ser  Ser  Ser  Ala  Glu  Asn  Thr  Arg  Gln  Asn  Gly
               165                      170                     175

Ser  Asn  Asp  Ser  Asp  Arg  Tyr  Ser  Asp  Asn  Glu  Glu  Asp  Ser  Lys  Ile
               180                      185                     190

Glu  Leu  Lys  Leu  Glu  Lys  Arg  Glu  Pro  Leu  Lys  Gly  Arg  Ala  Lys  Thr
          195                      200                     205

Pro  Val  Thr  Leu  Lys  Gln  Arg  Arg  Val  Glu  His  Asn  Gln  Ser  Tyr  Ser
     210                      215                      220

Gln  Ala  Gly  Ile  Thr  Glu  Thr  Glu  Trp  Thr  Ser  Gly  Ser  Ser  Lys  Gly
225                      230                 235                          240

Gly  Pro  Leu  Gln  Ala  Leu  Thr  Arg  Glu  Ser  Thr  Arg  Gly  Ser  Arg  Arg
                    245                 250                      255

Thr  Pro  Arg  Lys  Arg  Val  Glu  Thr  Ser  Glu  His  Phe  Arg  Ile  Asp  Gly
               260                      265                     270

Pro  Val  Ile  Ser  Glu  Ser  Thr  Pro  Ile  Ala  Glu  Thr  Ile  Met  Ala  Ser
          275                      280                     285

Ser  Asn  Glu  Ser  Leu  Val  Val  Asn  Arg  Val  Thr  Gly  Asn  Phe  Lys  His
     290                      295                      300

Ala  Ser  Pro  Ile  Leu  Pro  Ile  Thr  Glu  Phe  Ser  Asp  Ile  Pro  Arg  Arg
305                      310                 315                          320

Ala  Pro  Lys  Lys  Pro  Leu  Thr  Arg  Ala  Glu  Val  Gly  Glu  Lys  Thr  Glu
                    325                 330                      335

Glu  Arg  Arg  Val  Glu  Arg  Asp  Ile  Leu  Lys  Glu  Met  Phe  Pro  Tyr  Glu
               340                      345                     350

Ala  Ser  Thr  Pro  Thr  Gly  Ile  Ser  Ala  Ser  Cys  Arg  Arg  Pro  Ile  Lys
          355                      360                     365

Gly  Ala  Ala  Gly  Arg  Pro  Leu  Glu  Leu  Ser  Asp  Phe  Arg  Met  Glu  Glu
     370                      375                      380

Ser  Phe  Ser  Ser  Lys  Tyr  Val  Pro  Lys  Tyr  Val  Pro  Leu  Ala  Asp  Val
385                      390                 395                          400

Lys  Ser  Glu  Lys  Thr  Lys  Lys  Gly  Arg  Ser  Ile  Pro  Val  Trp  Ile  Lys
               405                      410                     415

Ile  Leu  Leu  Phe  Val  Val  Val  Ala  Val  Phe  Leu  Phe  Leu  Val  Tyr  Gln
          420                      425                     430

Ala  Met  Glu  Thr  Asn  Gln  Val  Asn  Pro  Phe  Ser  Asn  Phe  Leu  His  Val
          435                      440                     445

Asp  Pro  Arg  Lys  Ser  Asn
     450
```

( 2 ) INFORMATION FOR SEQ ID NO:5:

( i ) SEQUENCE CHARACTERISTICS:
        ( A ) LENGTH: 2392 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 241..1275

( x i ) SEQUENCE DESCRIPTION: SEQ ID NO:5:

```
CCCTGCTACC AAGGCCCAGC TATGGCCCCA GGGTTGAAAA GTTATGAGGG TCAGGGGTCT      60
TTTGTGTCCG GGTCTGGCTT GGCTTTGTGT CCGCGAGTTT TTGTTCCGCT CCGCAGCGCT     120
CTTCCCGGGC AGGAGCCGTG AGGCTCGGAG GCGGCAGCGC GGTCCCCGGC CAGGAGCAAG     180
CGCGCCGGCG TGAGCGGCGG CGGCAAAGGC TGTGGGGAGG GGGCTTCGCA GATCCCCGAG     240
ATGCCGGAGT TCCTGGAAGA CCCCTCGGTC CTGACAAAAG ACAAGTTGAA GAGTGAGTTG     300
GTCGCCAACA ATGTGACGCT GCCGGCCGGG GAGCAGCGCA AGACGTGTA  CGTCCAGCTC     360
TACCTGCAGC ACCTCACGGC TCGCAACCGG CCGCCGCTCC CCGCCGGCAC CAACAGCAAG     420
GGGCCCCCGG ACTTCTCCAG TGACGAAGAG CGCGAGCCCA CCCCGGTCCT CGGCTCTGGG     480
GCCGCCGCCG CGGGCCGGAG CCGAGCAGCC GTCGGCAGGA AGCCACAAA  AAAAACTGAT     540
AAACCCAGAC AAGAAGATAA AGATGATCTA GATGTAACAG AGCTCACTAA TGAAGATCTT     600
TTGGATCAGC TTGTGAAATA CGGAGTGAAT CCTGGTCCTA TTGTGGGAAC AACCAGGAAG     660
CTATATGAGA AAAAGCTTTT GAAACTGAGG GAACAAGGAA CAGAATCAAG ATCTTCTACT     720
CCTCTGCCAA CAATTTCTTC TTCAGCAGAA AATACAAGGC AGAATGGAAG TAATGATTCT     780
GACAGATACA GTGACAATGA AGAAGACTCT AAAATAGAGC TYAAGCTTGA GAAGAGAGAA     840
CCACTAAAGG GCAGAGCAAA GACTCCAGTA ACACTCAAGC AAAGAAGAGT TGAGCACAAT     900
CAGGTGGGAG AAAAAACAGA GGAAAGAAGA GTAGAAAGGG ATATTCTTAA GGAAATGTTC     960
CCCTATGAAG CATCTACACC AACAGGAATT AGTGCTAGTT GCCGCAGACC AATCAAAGGG    1020
GCTGCAGGCC GGCCATTAGA ACTCAGTGAT TCAGGATGG  AGGAGTCTTT TTCATCTAAA    1080
TATGTTCCTA AGTATGTTCC CTTGGCAGAT GTCAAGTCAG AAAAGACAAA AAAGGGACGC    1140
TCCATTCCCG TATGGATAAA AATTTTGCTG TTTGTTGTTG TGGCAGTTTT TTTGTTTTTG    1200
GTCTATCAAG CTATGGAAAC CAACCAAGTA AATCCCTTCT CTAATTTTCT TCATGTTGAC    1260
CCTAGAAAAT CCAACTGAAT GGTATCTCTT TGGCACGTTC AACTTGGTCT CCTATTTTCA    1320
ATAACTGTTG AAAAACATTT GTGTACACTT GTTGACTCCA AGAACTAAAA ATAATGTGAT    1380
TTCGCCTCAA TAAATGTAGT ATTTCATTGA AAAGCAAACA AAATATATAT AAATGGACTT    1440
CATTAAAATG TTTTTGAACT TTGGACTAGT AGGAGATCAC TTTGTGCCAT ATGAATAATC    1500
TTTTTTAGCT CTGGAACTTT TTGTAGGCTT TATTTTTTA  ATGTGGGCAT CTTATTTCAT    1560
TTTTGAAAAA ATGTATATGT TTTTGTGTA  TTTGGGAAAC GAAGGGTGAA ACATGGTAGT    1620
ATAATGTGAA GCTACACATT TAAATACTTA GAATTCTTAC AGAAAGATT  TTAAGAATTA    1680
TTCTCTGCTG AATAAAAACT GCAAATATGT GAAACATAAT GAAATTCAGT AAGAGGAAAA    1740
GTAACTTGGT TGTACTTTTT GTAACTGCAA CAAAGTTTGA TGGTGTTTAT GAGGAAAAGT    1800
ACAGCAATAA TCTCTTCTGT AACCTTTATT AATAGTAATG TTGTTGTAGC CCTATCATAC    1860
TCACTTTTTA AGACACAGTA TCATGAAAGT CCTATTTCAG TAAGACCCAT TTACATACAG    1920
```

| TAGATTTTTA | GCAGAGATCT | TTTAGTGTAA | CATACATATT | TTAGAGAATT | GTTGGCTAGC | 1980 |
| TGTACATGTT | TTGAAAAGCT | GTTTAGCTAG | CTATAAGGCT | ATAATTGGAA | ATTTGTATTT | 2040 |
| TTTATTTACA | GCAAAACATT | TATTCAGTCA | TCCAGTTTGC | TACCAAAATA | TGTTTAGAT | 2100 |
| AAGTGTGTGT | ATGTTTGTTT | AGAAGTTAGA | AATTGTAAAC | ACTGGTCTTA | TGTTTCATTT | 2160 |
| GGATTCATTA | TTGCATTGTC | TTGTTACCAG | AAACAAATTT | TGCCGAGCTT | TTTTGCCCT | 2220 |
| ATATTTCCCA | GCATAATTTG | ATTAGAAAGT | ACAAAAGGG | CCGGGCGCGG | TGGCTTACGC | 2280 |
| CTGTAATCCC | AGCACTTTGG | GAGGCCAGGG | CGGGTGGATC | ACGAGGTCAG | GAGATCGGGA | 2340 |
| CCATCCTGGC | CAACATGGTG | AAACCCCGTC | TCTACTAAAA | AAAAAAAAA | AA | 2392 |

( 2 ) INFORMATION FOR SEQ ID NO:6:

( i ) SEQUENCE CHARACTERISTICS:
        ( A ) LENGTH: 345 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

| Met | Pro | Glu | Phe | Leu | Glu | Asp | Pro | Ser | Val | Leu | Thr | Lys | Asp | Lys | Leu |
| 1 | | | | 5 | | | | | 10 | | | | | 15 | |
| Lys | Ser | Glu | Leu | Val | Ala | Asn | Asn | Val | Thr | Leu | Pro | Ala | Gly | Glu | Gln |
| | | | 20 | | | | 25 | | | | | 30 | | | |
| Arg | Lys | Asp | Val | Tyr | Val | Gln | Leu | Tyr | Leu | Gln | His | Leu | Thr | Ala | Arg |
| | | 35 | | | | 40 | | | | | 45 | | | | |
| Asn | Arg | Pro | Pro | Leu | Pro | Ala | Gly | Thr | Asn | Ser | Lys | Gly | Pro | Pro | Asp |
| | 50 | | | | 55 | | | | | 60 | | | | | |
| Phe | Ser | Ser | Asp | Glu | Glu | Arg | Glu | Pro | Thr | Pro | Val | Leu | Gly | Ser | Gly |
| 65 | | | | 70 | | | | | 75 | | | | | 80 | |
| Ala | Ala | Ala | Ala | Gly | Arg | Ser | Arg | Ala | Ala | Val | Gly | Arg | Lys | Ala | Thr |
| | | | | 85 | | | | | 90 | | | | | 95 | |
| Lys | Lys | Thr | Asp | Lys | Pro | Arg | Gln | Glu | Asp | Lys | Asp | Asp | Leu | Asp | Val |
| | | | 100 | | | | | 105 | | | | | 110 | | |
| Thr | Glu | Leu | Thr | Asn | Glu | Asp | Leu | Leu | Asp | Gln | Leu | Val | Lys | Tyr | Gly |
| | | | 115 | | | | | 120 | | | | | 125 | | |
| Val | Asn | Pro | Gly | Pro | Ile | Val | Gly | Thr | Thr | Arg | Lys | Leu | Tyr | Glu | Lys |
| | | 130 | | | | 135 | | | | | 140 | | | | |
| Lys | Leu | Leu | Lys | Leu | Arg | Glu | Gln | Gly | Thr | Glu | Ser | Arg | Ser | Ser | Thr |
| 145 | | | | | 150 | | | | | 155 | | | | | 160 |
| Pro | Leu | Pro | Thr | Ile | Ser | Ser | Ser | Ala | Glu | Asn | Thr | Arg | Gln | Asn | Gly |
| | | | | 165 | | | | | 170 | | | | | 175 | |
| Ser | Asn | Asp | Ser | Asp | Arg | Tyr | Ser | Asp | Asn | Glu | Glu | Asp | Ser | Lys | Ile |
| | | | 180 | | | | | 185 | | | | | 190 | | |
| Glu | Leu | Lys | Leu | Glu | Lys | Arg | Glu | Pro | Leu | Lys | Gly | Arg | Ala | Lys | Thr |
| | | 195 | | | | | 200 | | | | | 205 | | | |
| Pro | Val | Thr | Leu | Lys | Gln | Arg | Arg | Val | Glu | His | Asn | Gln | Val | Gly | Glu |
| | 210 | | | | | 215 | | | | | 220 | | | | |
| Lys | Thr | Glu | Glu | Arg | Arg | Val | Glu | Arg | Asp | Ile | Leu | Lys | Glu | Met | Phe |
| 225 | | | | | 230 | | | | 235 | | | | | | 240 |
| Pro | Tyr | Glu | Ala | Ser | Thr | Pro | Thr | Gly | Ile | Ser | Ala | Ser | Cys | Arg | Arg |
| | | | | 245 | | | | | 250 | | | | | 255 | |
| Pro | Ile | Lys | Gly | Ala | Ala | Gly | Arg | Pro | Leu | Glu | Leu | Ser | Asp | Phe | Arg |
| | | | 260 | | | | | 265 | | | | | 270 | | |
| Met | Glu | Glu | Ser | Phe | Ser | Ser | Lys | Tyr | Val | Pro | Lys | Tyr | Val | Pro | Leu |

```
                              275                        280                           285
    Ala  Asp  Val  Lys  Ser  Glu  Lys  Thr  Lys  Lys  Gly  Arg  Ser  Ile  Pro  Val
         290                       295                      300

Trp  Ile  Lys  Ile  Leu  Leu  Phe  Val  Val  Val  Ala  Val  Phe  Leu  Phe  Leu
    305                       310                      315                           320

Val  Tyr  Gln  Ala  Met  Glu  Thr  Asn  Gln  Val  Asn  Pro  Phe  Ser  Asn  Phe
                        325                      330                           335

Leu  His  Val  Asp  Pro  Arg  Lys  Ser  Asn
                        340                      345
```

( 2 ) INFORMATION FOR SEQ ID NO:7:

( i ) SEQUENCE CHARACTERISTICS:
       ( A ) LENGTH: 52 amino acids
       ( B ) TYPE: amino acid
       ( D ) TOPOLOGY: unknown ( i i ) MOLECULE TYPE: protein ( x i ) SEQUENCE DESCRIPTION: SEQ ID NO:7:

```
    Pro  Glu  Phe  Leu  Glu  Asp  Pro  Ser  Val  Leu  Thr  Lys  Asp  Lys  Leu  Lys
    1                        5                       10                            15

Ser  Glu  Leu  Val  Ala  Asn  Asn  Val  Thr  Leu  Pro  Ala  Gly  Glu  Gln  Arg
                        20                      25                       30

Lys  Asp  Val  Tyr  Val  Gln  Leu  Tyr  Leu  Gln  His  Leu  Thr  Ala  Arg  Asn
                   35                       40                      45

Arg  Pro  Pro  Leu
                   50
```

METHOD FOR THE DIAGNOSIS OF DEPRESSION BASED ON MONITORING BLOOD LEVELS OF ARGININE VASOPRESSIN AND/OR THYMOPOIETIN

FIELD OF THE INVENTION

The present invention relates generally to methods for diagnosis of disorders characterized by depression and stress. More particularly, the invention provides a novel means of making or confirming a diagnosis of an affective disorder, such as depression, based on the blood levels of arginine vasopressin and thymopoietin, either individually or in combination.

BACKGROUND OF THE INVENTION

A. Arginine vasopressin

*Arginine vasopressin* (AVP), a neurohormone also known as anti-diuretic hormone, is characterized by a nine amino acid, partially cyclic structure. AVP has been reported to be associated in serum with a binding protein, called neurophysin [Brain Peptides, (D. T. Krieger et al, eds.), John Wiley & Sons, New York, pp. 598–611 (1983)]. AVP is secreted from two major locations in the brain, from hypothalamic parvicellular neurons in the paraventricular nucleus, which also produce corticotropin releasing factor (CRF), and from magnocellular neurons in the supraoptic and paraventricular nuclei [F. A. Antoni, in *Frontiers in Neuroendocrinology*, 14(2):76–122 (1993)]. CRF is known to synergize with AVP to stimulate ACTH release.

It has been demonstrated that, following the application of chronic stress paradigms in laboratory animals, there is an increase in the level of AVP in the paraventricular nucleus of the hypothalamus. This AVP level is disproportionately large compared with the increase observed in CRF levels [Antoni, cited above; D. C. De Goeij et al, *Endocrinol.*, 131:847 (1992)]. Following chronic stress, AVP levels within CRF-containing neurons within the paraventricular nucleus of the hypothalamus of laboratory animals have been reported to increase by over 8 fold, while the increase in CRF levels was 1.5 fold. This disproportionate increase in the level of AVP in this portion of the hypothalamus as compared with CRF has also been observed to be maintained at the level of the median eminence, the terminal bed from which AVP and CRF are released to stimulate ACTH secretion from the pituitary.

Previous attempts have been made to correlate altered plasma levels of both CRF and AVP with psychiatric disorders, such as depression, in humans. However, attempts to establish a diagnostic evaluation of such conditions by measuring blood levels of AVP have been unsuccessful. Such efforts have reported either no difference in AVP levels between depressed patients and normal controls, or a decrease in cerebrospinal fluid (CSF) AVP levels caused by depression. For example, P. S. Sorensen et al., *J. Neurol. Neurosurg. Psych.*, 48:50–57 (1985) found no difference in AVP levels in the plasma of depressed patients vs. normal controls.

In a study by P. W. Gold et al., *Psychopharmacol. Bull.*, 19:426–431 (1983), decreases in AVP below the control levels in CSF were found in non-psychotic depressed patients. Other researchers have attempted to correlate AVP levels in CSF and in plasma for depressed patients and have found a decrease in CSF AVP, but no difference in plasma AVP [A. Gjerris et al, *Brit. J. Psychiatry*, 147:696–701 (1985)]. A more recent study of AVP levels in the CSF of depressed patients vs. normal controls also revealed a decrease in AVP levels for such patients [A. Gjerris, *Acta Psychiatr. Scand.*, 78, Suppl. 345:21–24 (1988)]. To date, no one has ever reported an increase in plasma AVP levels in depression.

Blood levels of AVP have been studied most extensively in relation to water and electrolyte balance in the body. For example, a lack of AVP is associated with diabetes insipidus, which causes a failure to retain fluid by the kidneys and a resultant decrease in electrolytes. This condition is treated by the administration of AVP. There is also a rare syndrome of elevated AVP in blood, referred to as the syndrome of inappropriate antidiuretic hormone secretion (SIADH). See, e.g., S. Hou, "Syndrome of Inappropriate Antidiuretic Hormone Secretion" in Reichlin S., ed., *The Neurohypophysis*, Plenum Press, New York (1984) pp. 166–189. Occasionally, an excess of AVP has been found associated with certain cancers, such as malignant neoplasias, lymphomas, leukemias, thymomas and mesotheliomas. Inappropriate AVP levels have also been observed in rare cases of pulmonary disorders such as tuberculosis and pneumonia and in central nervous system disorders such as trauma. Abnormal AVP levels have also been noted as a consequence of drugs that enhance AVP release or action, e.g., diuretics.

However, the changes or elevations of AVP blood levels in these relatively rare conditions are accompanied by physiologic symptoms and changes in serum electrolytes, and are thus clearly distinguishable by the context in which such elevation is observed [See, e.g., *Textbook of Endocrinology*, 7th ed. (Wilson and Foster, eds) 1985 pp. 644–645]. Such increases in AVP have been detected by radioimmunoassay.

B. Thymopoietin

The thymic hormone thymopoietin (TP) has been shown to play a regulatory role in immune, nervous, and endocrine functions and has been isolated from bovine and human thymus. For additional general information on TP, see, also, G. H. Sunshine et al, *J. Immunol.*, 120:1594–1599 (1978); G. Goldstein, *Nature*, 247:11–14 (1974); D. H. Schlesinger and G. Goldstein, *Cell*, 5:361–365 (1975); G. Goldstein et al., *Lancet* 2:256–262 (1975). TP has also been found to be present in brain extracts [R. H. Brown, et al., *Brain Research* 381:237–243 (1986)].

It has been found that as the thymus involutes with age, thymic hormone levels decrease, which is believed to be related to increased susceptibility to disease in aging [G. Goldstein and I. R. Mackay, *The Human Thymus*, Wm. Heineman Med. Books Ltd., London (1969)]. Additionally, hypersecretion of TP has been implicated in myasthenia gravis [G. Goldstein, *Lancet*, 2:1164–1167 (1966)], as being involved in the impairment of signal transmission from nerve to muscle. When this signal is interrupted, the result is generalized weakness.

Previous attempts to measure TP levels by bioassay have suggested various differences in TP levels in different pathological states. However, to date, no one has provided any correlation between affective disorders and TP.

Bioassays used to measure TP are cumbersome, inaccurate and unreliable. [J. J. Twomey, et al., *Proc. Natl. Acad. Sci. USA*, 74:2541–2545 (1977); V. M. Lewis, et al., *J. Clin. Endo. Metab.* 47:145–150 (1978); J. J. Twomey, et al., *Am. J. Med.* 68:377–380 (1980)]. Immunoassays are the preferred format for measuring peptides and proteins in plasma or serum, but prior attempts to develop immunoassays to measure TP have not yielded clinically useful techniques. For example, a displacement radioimmunoassay (RIA) for measuring bovine TP was developed that detected TP concentrations greater than 5 ng/mL in tissue extracts. However this RIA is incapable of measuring TP levels in blood [see, e.g., G. Goldstein, *J. Immunol.* 117:690–692 (1976)].

The sensitivity of the TP RIA was subsequently increased to 20 picograms (pg) [see, e.g., P. J. Lisi et al, *Clin. Chim. Acta*, 107:111–119 (1980)] using "human serum-based standards" and rabbit antisera. However, this assay has not proved effective or reproducible in practice. In addition, the present inventors have found that 20 picograms sensitivity is too poor to detect human blood levels of TP. A sandwich enzyme-linked immunoassay (ELISA) was later developed for bovine TP using a combination of polyclonal and monoclonal antibodies [A. Fuccello et al, *Arch. Biochem. Biophys.*, 228:292–298 (1984)]. Although the assay provided specificity in distinguishing bovine TP from bovine splenin, it proved ineffective in measuring TP in humans.

Direct measurement of TP in human plasma or serum has not been accurately reported. Possible reasons for this problem may include aggregation of TP with either itself or other blood proteins, complexing of TP with specific proteins, and too low a concentration of TP to be detected by standard assay methods.

There remains a need in the art for the development of reliable methods based on blood levels of AVP and/or TP, which enable the laboratory diagnosis or confirmation of affective disorders, such as depression and/or anxiety, in humans.

SUMMARY OF THE INVENTION

In one aspect, the present invention provides a method for the laboratory diagnosis (or confirmation of diagnosis) of affective disorders, including depression, anxiety and stress, which is based upon detection of an increase in blood levels of AVP, particularly plasma or serum levels. The increase is significant when compared to a normal AVP range for non-depressed subjects.

In another aspect, the present invention provides a method for the laboratory diagnosis (or confirmation of diagnosis) of affective disorders, including depression, anxiety and stress, which is based upon detection of an increase in blood levels of TP, particularly plasma or serum levels. The increase is significant when compared to a normal TP range for non-depressed subjects.

In yet a further aspect, the present invention provides a method for the laboratory diagnosis (or confirmation of diagnosis) of affective disorders, including depression, anxiety and stress, which is based upon detection of an increase in blood levels of both AVP and TP values, taken in combination, particularly plasma or serum levels. The increase is significant when compared to a normal range of combined AVP/TP values for non-depressed subjects.

In still another aspect, the invention provides a diagnostic kit for the diagnosis of depression, anxiety and stress, providing the components necessary for the detection of elevated blood levels of AVP and/or TP.

Other aspects and advantages of the present invention are described further in the following detailed description of the preferred embodiments thereof.

BRIEF DESCRIPTION OF THE DRAWINGS

FIG. 5 is tabular evaluation of the discrimination of TP, AVP and combined measurements in depressed and control subjects when samples were obtained in the afternoon.

DETAILED DESCRIPTION OF THE INVENTION

Figure 1:
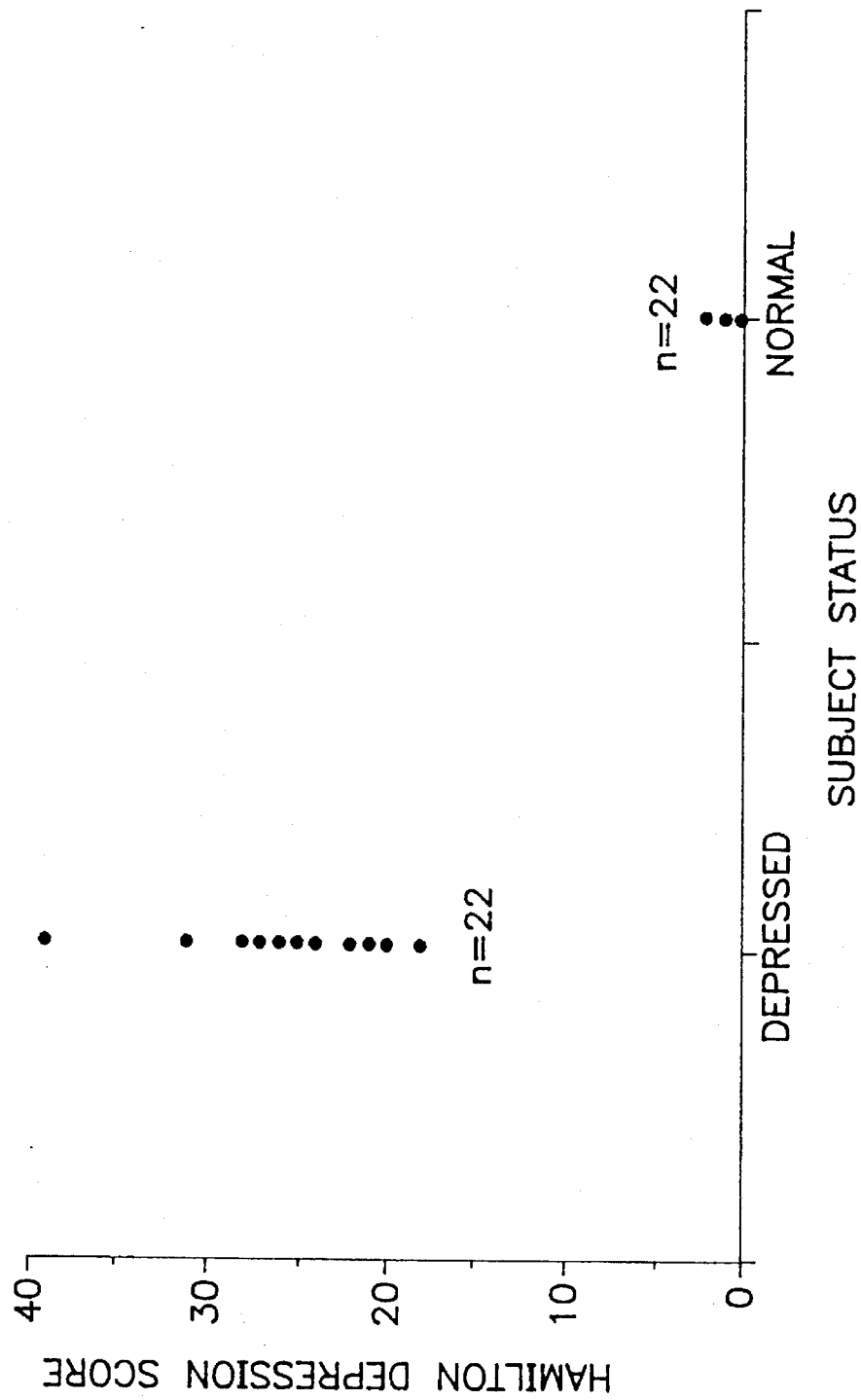
FIG. 1 is a graph plotting Hamilton Depression Scores for the subjects used in the examples. See, Example 1.

The present invention provides methods and laboratory kits which are useful for diagnosing affective disorders, such as depression, anxiety and stress, and/or for confirming a diagnosis of such an affective disorder. As used herein, the term "affective disorder" has its conventional meaning in psychiatry and encompasses such illnesses as chronic or major depression, anxiety, stress, and eating disorders, among others.

The methods of this invention are based on the discovery by the inventors that in a subject with depression, the level(s) of arginine vasopressin and/or thymopoietin in plasma or serum detectably and significantly increases.

I. Methods based on AVP Measurement

Without wishing to be bound by theory, the inventors determined that increased levels of AVP in blood might be a useful clinical marker of chronic stress and related affective illnesses, such as major depression in humans. Despite the contradictory teachings of the art concerning the lack of utility of measuring levels of AVP in blood during depression or stress (see, e.g., Sorenson et al, Gold et al, and Gjerris et al, cited above), the inventors created the novel diagnostic method of the present invention. As embodied in the examples below, the inventors have demonstrated by comparing AVP levels in clinically depressed subjects with normal subjects, that the detection of elevations in AVP blood levels beyond a normal range provides a reliable diagnostic indication of an affective disorder.

Further, while significantly elevated AVP levels were observed in depressed subjects both in the morning and in the afternoon, it was found that the afternoon levels were a more powerful predictor of affective illness. See, e.g., FIG. 5. Despite this observation, the invention is not limited to the detection of elevated AVP levels in the afternoon. Other times may also be advantageous in obtaining measurements of AVP as a predictor of affective illness, for example, early morning or late evening AVP levels.

Thus, the invention provides a new method for confirming or initially diagnosing an affective disorder, which entails measuring AVP levels in human blood and comparing the measured levels to a laboratory range for normal human AVP levels. This measurement of the increase in AVP may be readily made by use of a suitable immunoassay, in concert with an extraction or dissociation technique to separate the AVP from its neurophysin prior to measurement. One such assay format for the measurement of AVP in plasma or in the cerebrospinal fluid is the radioimmunoassay disclosed by M. Hammer, *Scand. J. Clin. Lab. Invest.*, 38:707–716 (1978), incorporated by reference herein.

According to the method of the invention, such an immunoassay is employed to evaluate a subject, preferably a human subject, for an affective disorder, e.g., depression. Briefly described, a plasma sample is prepared by taking a blood sample from a patient in the presence of an anticoagulent and separating the plasma from other components in the sample by conventional conditions. Such conditions may be selected by one of skill in the art, but can include, for example, centrifugation at a rate of about 1150×g for about 20 minutes. The AVP in the sample is dissociated from its binding protein, neurophysin, by use of known dissociation methods, such as acidification or extraction of the plasma with ethanol. However, one skilled in the art may employ other conventional dissociation methods for the same purpose.

The AVP protein is then separated from the neurophysin by conventional techniques, which are determined by the method of dissociation employed. For example, in the case of ethanol extraction, the denatured neurophysin is collected as a pellet by centrifugation using conventional conditions, such as centrifugation at about 2000×g for about 15 minutes at 4° C. The supernatant containing the free AVP is removed and evaporated under nitrogen, resulting in a dried sample containing the free AVP. It should be noted that one skilled in the art may employ other conventional extraction methods for the same purpose.

This sample is then preferably assayed by one of several conventional AVP immunoassay methods, such as that described by M. Hammer, cited above and incorporated by reference herein. Similarly a commercial kit useful in this method is a radioimmunoassay from Diagnostic Systems Laboratories, Inc., Webster, Tex. Other similar AVP assays and kits may also be employed.

Using such a method, a sample of plasma, taken from the patient at one or more time points, is assayed for AVP levels. The AVP levels of the patient are compared to the range of AVP levels observed in normal subjects. A diagnosis of depression is indicated when the AVP levels of the test subject are statistically elevated above the AVP levels of the normal range. It should be readily understood by one skilled in the art that normally such ranges are established independently by each testing laboratory to provide for any fluctuations in values caused by the way one particular laboratory performs the test, the characteristics of the antibodies used and any slight alterations in the assay format used. For example, the afternoon level of plasma AVP observed in normal subjects in Example 2 in the inventor's laboratory, using a commercial AVP RIA kit (Diagnostic Systems Laboratories, Webster, Tex.) was about 2.7±1.3 pg/ml (mean±standard deviation) and ranged from about 0.5 to about 5.4 pg/ml.

As demonstrated by Example 2 below, a diagnosis of depression is indicated when the AVP levels of the test subject are greater than the statistically determined range of AVP levels for normal subjects as determined by the laboratory performing the test. For example, the afternoon level of plasma AVP observed in depressed subjects in the inventors' laboratory, using a commercial AVP RIA kit was about 5.0±2.4 pg/ml (mean±standard deviation) and ranged from about 1.4 to about 13.2 pg/ml. When analyzed by a logistic regression model, which is used to differentiate two populations [see, e.g., D. Hosmer and S. Lemeshow, "Applied Logistic Regression" Wiley & Sons, New York (1989)] a "cutoff" level of 3.6 pg AVP/ml plasma was determined.

Thus, for this experiment in the inventors' laboratory and using the stated methods, an individual whose plasma AVP level is less than 3.6 pg/ml would be considered normal, while an individual whose plasma AVP level is greater than 3.6 pg/ml would be considered depressed. A slight overlap of the AVP levels in the normal and depressed populations represents potential false positive and false negative determinations. For Example 2, the false positive estimate is 24% and the false negative estimate is 19% for afternoon measurements of AVP.

This method may be performed as a primary diagnostic method or, preferably, it may be performed to confirm a preliminary diagnosis of a selected affective disorder based on psychological or behavioral symptoms. Because such symptoms can be related to other disorders than depression, the method of this invention provides a much needed laboratory diagnostic tool for depression and other affective disorders. This method has preliminarily been found to have at least an 81% success rate in diagnosing depression. It is further anticipated that other affective disorders will correlate with analogous levels of AVP. Additionally the method of this invention may also be employed to monitor the progress of treatment of depression, i.e., to show that the subject is approaching normal AVP levels as treatment is ongoing.

II. Methods based on TP Measurement

In still another embodiment of this invention, a novel method for making or confirming a diagnosis of an affective disorder such as depression, entails measuring TP levels in human blood and comparing the measured levels to a laboratory range for normal human TP levels. The inventors have found that elevated plasma or serum levels of TP are also found in depressed subjects.

Without wishing to be bound by theory, the inventors determined that increased levels of TP in blood might be a useful clinical marker of chronic stress and related affective illnesses, such as major depression in humans. Despite the dearth of teachings of the art concerning the any utility in measuring levels of TP in blood during depression or stress, the inventors have devised the novel diagnostic method of the present invention. As embodied in the examples below, the inventors have demonstrated by comparing TP levels in clinically depressed subjects with normal subjects, that the detection of elevations in TP blood levels beyond a normal range provides a reliable diagnostic indication of an affective disorder.

Further, while significantly elevated TP levels were observed in depressed subjects both in the morning and in the afternoon, it was found that the afternoon levels were a more powerful predictor of affective illness. See, e.g., FIG. 5. Despite this observation, the invention is not limited to the detection of elevated TP levels in the afternoon. Other times may also be advantagous in obtaining measurements of TP as a predictor of affective illness, for example, early morning or late evening TP levels.

Thus, the invention provides a new method for confirming or initially diagnosing an affective disorder, which entails measuring TP levels in human blood and comparing the measured levels to a laboratory range for normal human TP levels. This measurement of the increase in TP may be readily made by use of a suitable immunoassay which enables detection of TP at a sensitivity greater than 20 pg/ml. Such an immunoassay may include an optional extraction or dissociation technique to separate the TP from any other protein with which it may be bound in circulation prior to measurement, such as the techniques described in co-owned, concurrently filed, U.S. Patent Application entitled "Method of Measuring Thymopoietin Proteins in Plasma and Serum" and incorporated by reference herein.

This sample is preferably assayed by a suitable assay for the measurement of TP. See, e.g., the above-referenced patent application. As described therein, TP may be measured in plasma and serum following dissociation of TP from any plasma protein complexes, and subsequent extraction. Alternatively, TP may be measured directly in plasma or serum by using the assay capable of detecting TP in human blood at levels well below 20 pg/ml.

According to the method of the invention, such an immunoassay is employed to evaluate a subject, preferably a human subject, for an affective disorder, e.g., depression. Briefly described, a plasma sample is prepared by taking a blood sample from a patient in the presence of an anticoagulent, e.g., EDTA or heparin, and separating the plasma from other components in the sample by conventional conditions. Such conditions may be selected by one of skill in the art, but can include, for example, centrifugation at a rate of about 1150×g for about 20 minutes.

According to one aspect of this method, the conditions for the first step, i.e., dissociating the TP from any complex, involves acidifying the serum or plasma sample sufficiently to effect the dissociation of bound TP from a protein complex. Generally, the sample is acidified with a selected acid to provide a sample pH of less than about 3. However, it is anticipated that partial and, eventually, complete dissociation may be achieved at other sample pH levels less than neutral. A presently preferred acid for use in this acidification/extraction step is trifluoroacetic acid (TFA). Other acids which may be substituted for TFA include, without limitation, mineral acids, such as hydrochloric, nitric and sulfuric acid.

Once the TP is so dissociated, it may be extracted from the sample in order to prevent reaggregation that may potentially interfere with subsequent assay of TP content. A presently preferred method for the extraction of free TP is through the use of a C-18 reverse phase cartridge. The presently preferred method utilizes C-18 SepPak® cartridges (™Waters, a Division of the Millipore Corp.). The SepPak® cartridge is activated by the sequential passage through the cartridge of deionized, distilled water, a 20:80 ratio of 0.1% TFA:acetonitrile for TP extraction, and 0.1% TFA alone in sufficient quantities to achieve full activation. Desirably, the free TP, now bound to the C-18 matrix, is eluted with an appropriate ratio of TFA:acetonitrile containing 0.01% Tween® 20 reagent. The elution is preferably performed using a 20:80 ratio of 0.1% TFA:acetonitrile and the eluted, free TP is contained in the 20:80 mixture. Alternatively, other methods to extract free TP from potentially interfering plasma substances may include without limitation, high-performance liquid chromatography (HPLC), size-exclusion chromatography, ion exchange chromatography, dye-ligand chromatography, affinity chromatography, lectin-carbohydrate binding matrixes, solvent extractions, ultrafiltration, dialysis, etc.

The TFA and acetonitrile present in the sample following the extraction step described above must be separated from the TP prior to assay in order to prevent interference of these solvents with the assay reagents. The presently preferred method of removing acetonitrile is to evaporate the eluted solvent in a heated block (about 40° C.) under a stream of nitrogen gas. The evaporation is preferably performed to at least about 20% of the original, eluted volume. Alternatively, other conditions known to those of skill may be employed to prepare the extracted TP for assay.

The free TP now substantially free of protein complexes, and interfering materials, e.g., solvents and reagents used for extraction, are placed into a medium suitable for use in the assay of choice. The presently preferred assay medium is 0.05M phosphate buffered physiologic saline (PBS) containing 0,025M ethylenediaminetetraacetic acid (EDTA), 0.04% sodium azide, 1% bovine serum albumin, and 0.1% Tween® 20 reagent. Alternatively, other media known to those of skill in the art may be employed.

The extracted plasma/serum sample now suspended in an appropriate assay medium can be assayed for the mass of total TP, a specific TP form (e.g. α [SEQ ID NO: 2], β [SEQ ID NO: 4], or γ [SEQ ID NO: 6]), or a circulating TP molecule derived from one of these proteins. The presently preferred method of quantitating TP is the use of an enzyme-linked immunoassay. However, other appropriate assay methods may be selected, e.g. fluorescence assays such as those employing europium, electrophoretic methods, receptor assays, bioassays, and mass spectroscopy. One particularly desirable and sensitive assay for the measurement of TP in the serum/plasma extract is enzyme-linked "sandwich" immunoassay (ELISA).

The sample is then preferably assayed by a conventional TP immunoassay method. The presently preferred method of quantitating TP is by an enzyme-linked immunoassay [C. P. Price et al (edso), "Principles and Practice of Immunoassay" Stockton Press, New York, N.Y. (1991)]. Other appropriate assay methods may be selected, e.g., fluorescence assays such as those employing europium, electrophoretic methods, receptor assays, bioassays, and mass spectroscopy.

Using such a method, a sample of plasma, taken from the patient at one or more time points, is assayed for TP levels. The TP levels of the patient are compared to the range of TP levels observed in normal subjects. A diagnosis of depression is indicated when the TP levels of the test subject are statistically elevated above the TP levels of the normal range. It should be readily understood by one skilled in the art that normally such ranges are established independently by each testing laboratory to provide for any fluctuations in values caused by the way one particular laboratory performs the test, the characteristics of the antibodies used and any slight alterations in the assay format used. For example, the afternoon level of plasma TP observed in normal subjects in Examples 3 and 3A in the inventor's laboratory ranged from about 2.5 to about 7.9 pg/ml, with a mean±standard deviation of 5.3±1.5 pg/ml.

As demonstrated by Example 3 below, a diagnosis of depression is indicated when the TP levels of the test subject are greater than the statistically determined range of TP levels for normal subjects as determined by the laboratory performing the test. For example, the afternoon level of plasma TP observed in depressed subjects in the inventors' laboratory, using the immunoassay described above ranged between about 3.1 and 13.1 pg/ml, with a mean (±standard deviation) level of 7.8±2.5 pg/ml. When analyzed by the logistic regression model referred to above, which is used to differentiate two populations, a "cutoff" level of 6.4 pg TP/ml plasma was determined.

Thus, for this experiment in the inventors' laboratory and using the stated methods, an individual whose plasma TP level is less than 6.4 pg/ml would be considered normal, while an individual whose plasma TP level is greater than 6.4 pg/ml would be considered depressed. A slight overlap of the TP levels in the normal and depressed populations represents potential false positive and false negative determinations. For Example 3, the false positive estimate is 19% and the false negative estimate is 24% for afternoon measurements of TP.

This method may be performed as a primary diagnostic method or, preferably, it may be performed to confirm a preliminary diagnosis of a selected affective disorder based on psychological or behavioral symptoms. Because such symptoms can be related to other disorders than depression, the method of this invention provides a much needed laboratory diagnostic tool for depression and other affective disorders. This method has preliminarily been found to have at least a 76% success rate in diagnosing depression. It is further anticipated that other affective disorders will correlate with analogous levels of TP. Additionally the method of this invention may also be employed to monitor the progress of treatment of depression, i.e., to show that the subject is approaching normal TP levels as treatment is ongoing.

III. Method Combining the AVP/TP Scores

As yet another embodiment of this invention, a novel method for making, or confirming a diagnosis of an affective disorder, such as depression, involves utilizing the AVP measurements, as described above, and the TP measurements, as described above, in the plasma or serum of a subject. While both measurements of AVP and TP levels independently show elevation in major depression, together they provide even greater discrimination in distinguishing subjects with depression from normal controls. Thus, this method can be an even more accurate predictor of an affective disorder.

Subjects were scored as depressed according to this invention when the AVP and TP results obtained in the individual assays described above were combined by a conventional statistical formula for logistical regression analysis using two parameters, i.e., both AVP and TP scores [Hosmer et al, cited above].

For example, using the scores obtained in Examples 2 and 3 discussed herein, a linear discriminant analysis, which confirmed the results of the logistic regression analysis, produced a straight line corresponding to the appropriate statistical formula. According to this analysis combining the individual AVP and TP scores, a subject was categorized as depressed with a combination score of greater than about 10.0 pg/ml. See, e.g., FIG. 4.

This combined method may be performed as a primary diagnostic method or, preferably, it may be performed to confirm a preliminary diagnosis of a selected affective disorder based on psychological or behavioral symptoms. Because such symptoms can be related to other disorders than depression, the method of this invention provides a much needed laboratory diagnostic tool for depression and other affective disorders. This method of using combined AVP and TP levels in this formula has preliminarily been found to have at least 81% success in correctly identifying depressed subjects and 90% success in correctly identifying normal controls. It is further anticipated that other affective disorders will correlate with analogous evaluations of the combined levels of AVP and TP. Additionally the method of this invention may also be employed to monitor the progress of treatment of depression, i.e., to show that the subject is approaching normal AVP and TP levels as treatment is ongoing.

IV. Diagnostic Kits of the Invention

Another embodiment of this invention is a diagnostic laboratory kit containing the essential components necessary for the performance of the assays of this invention. Such a kit includes reagents and hardware necessary to extract AVP from its neurophysin, anti-AVP antibodies and conventional immunoassay components for the measurement of AVP and a normal range of AVP levels in controls. Also included may be other conventional components, e.g., means for withdrawal of blood and vials for the collection and separation of blood components.

Additionally, such a kit may include reagents and hardware necessary to extract TP, anti-TP antibodies and conventional immunoassay components for the measurement of TP and a normal range of TP levels in controls. Further, such a kit may include reagents and equipment necessary to measure both AVP and TP levels in plasma or serum, as well as a normal range for both hormones, either alone or in combination.

The following examples illustrate preferred methods for diagnosing depression based on the method of this invention. The examples are illustrative only and do not limit the scope of the invention.

EXAMPLE 1

Identification, Enrollment and Blood Sampling of Patients Suffering from Major Depression and Normal Age/Sex Matched Control Subjects Normal (control) and depressed individuals who were age matched (±2 years) and sex matched formed the study population of interest. Patients were diagnosed as moderately to severely depressed based on criteria that fulfill the DSM-III-R (Diagnostic and Statistical Manual of Mental Disorders—Third Edition—Revised; American Psychiatric Association, 1987) criteria for current major depressive episodes, including a Hamilton Depression Rating$\geq 20$ and a Raskin Depression Score$\geq 7$.

Normal subjects were also screened using the DSM-III criteria to verify the absence of affective illness. The Hamilton Depression Ratings obtained for both the depressed and normal subjects used in the examples are illustrated in FIG. 1. Symptoms must have been present for a minimum of one month prior to entry in the study. Patients with current or past diagnosis of psychotic disorders, mania or hypomania, organic brain syndrome, mental retardation or dysthymia were excluded. The diagnosed patients were untreated for depressive symptoms prior to and during inclusion in the study. A total of 22 age/sex matched pairs of depressed patients and normal controls were obtained for the study.

Blood samples were withdrawn from the depressed and normal control subjects between 8 and 9 a.m. and again between 4 and 6 p.m. Blood samples were collected into ethylenediaminetetraacetic acid (EDTA) containing Vacutainer™ (Becton-Dickinson) tubes and placed on ice. Plasma was separated by centrifugation at 1150×g for 20 minutes and stored frozen (−70° C.) until assay.

EXAMPLE 2

Demonstration of Elevated AVP in Clinically Depressed Subjects

AVP was extracted from each plasma sample of each subject of Example 1 by mixing 800 µl plasma with 5 ml 4°

C. ethanol and inverting the tube end-over-end for 30 minutes at 4° C. The sample was centrifuged for 15 minutes at 2000×g at 4° C. to pellet the denatured protein. The supernatant was decanted and evaporated under a stream of nitrogen in a heated block.

The dried sample was resuspended in 0.8 ml assay buffer and the quantity of AVP was determined using a commercial AVP radioimmunoassay kit [Diagnostic Systems Laboratories, Inc., Webster, Tex.]

Figure 2A:
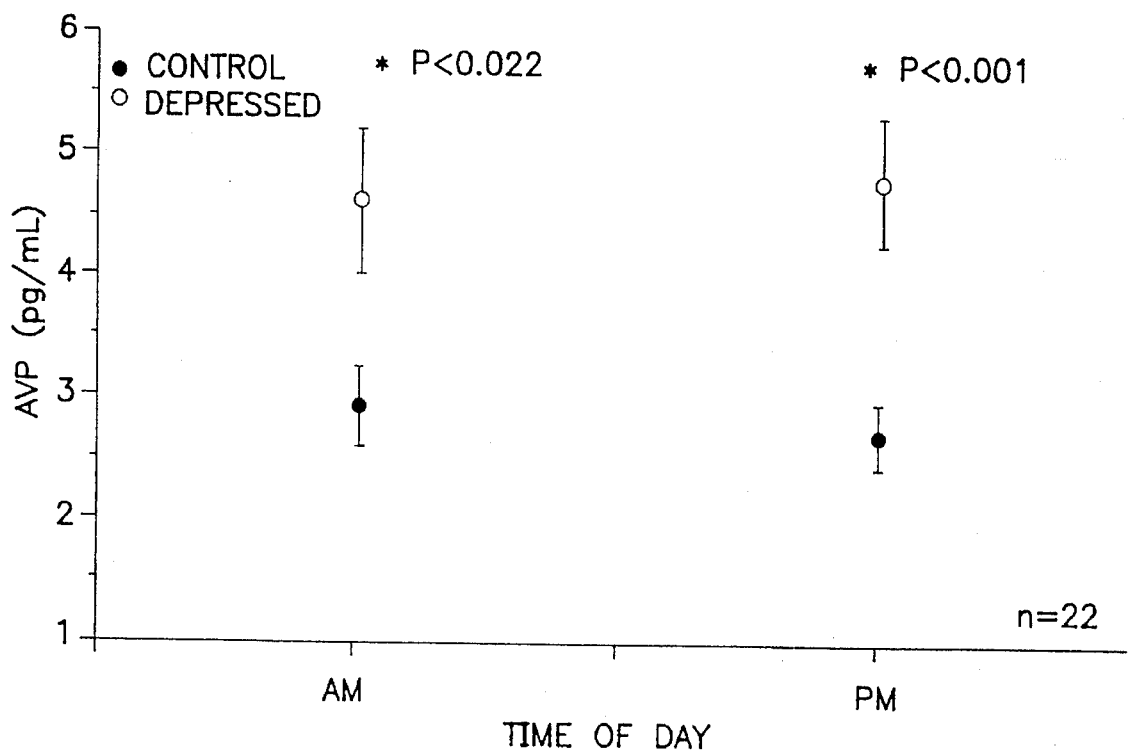
FIG. 2A is a graph plotting AVP levels in pg/ml vs. time of day which illustrates the differences in mean (±SEM) AVP levels between patients diagnosed as clinically depressed (open circle) and age/sex matched normal subjects (closed circle) at two different times of day. See, Example 2.

FIG. 2A plots the AVP levels in pg/ml vs. time of day, illustrating the differences in mean (±SEM) AVP levels between patients diagnosed as clinically depressed (open circle) and age/sex matched control subjects (closed circle) at two different times of day. The results demonstrate elevated AVP levels in patients diagnosed as clinically depressed at both morning (a.m.) and afternoon (p.m.) time points. The symbol, *, denotes a significant difference from control subjects drawn at the same time point.

Measurable levels of AVP were detected in all subjects. The mean AVP measurement obtained from normal control subjects was 2.7±1.3 pg/mL (mean±SD) and ranged between 0.5 and 5.4 pg/mL. However, the levels of AVP in the depressed subjects were significantly higher than those in control subjects at both the morning ($p<0.02$) and afternoon ($p=0.001$) time points. The mean AVP in depressed patients was 5.0±2.4 pg/ml (mean±SD) and ranged from 1.4 to 13.2 pg/mL.

A logistic regression model [see, Hosmer et al, cited above] was used to differentiate control and depressed individuals. The model determines the probability that an individual falls into either group. The logistic equation is solved for the AVP level which provides the greatest discrimination between the two groups. In the present example, this level was determined to be 3.6 pg AVP/mL for afternoon values. Using 3.6 pg/mL as the diagnostic criterion, individuals whose AVP levels are greater than 3.6 pg/mL are classified as 'depressed' and those whose AVP levels are less than 3.6 pg/mL are classified as 'normal'.

Figure 2B:
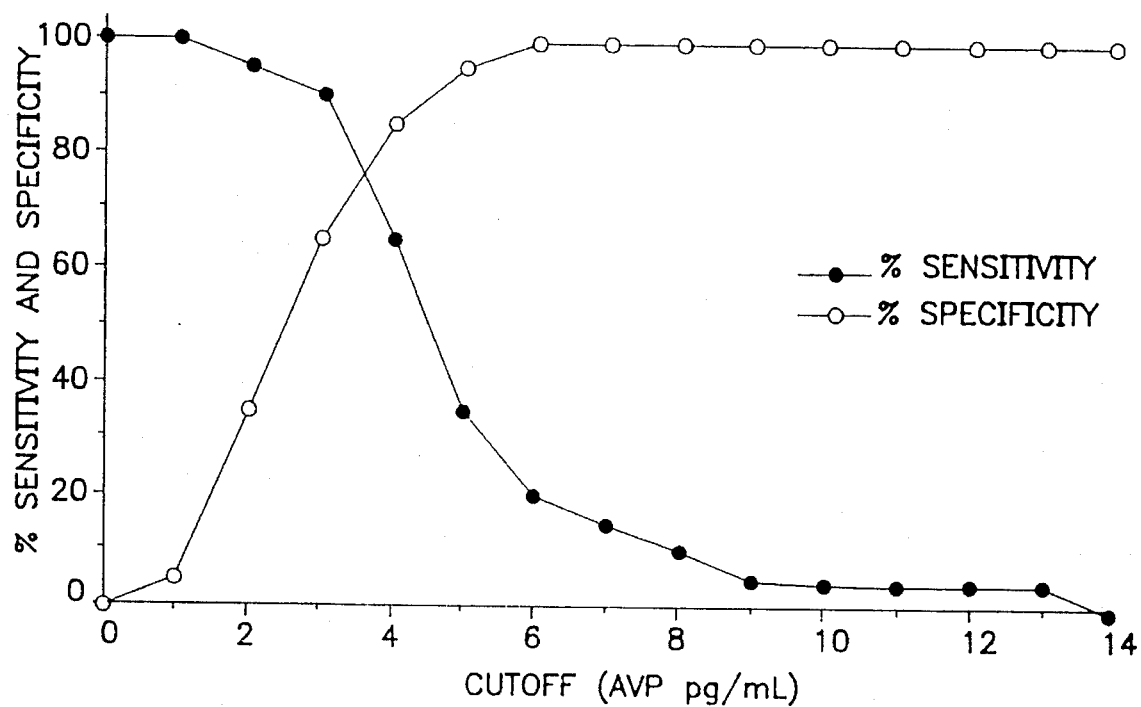
FIG. 2B is a graph plotting the sensitivity (false negative index) and the specificity (false positive index) for afternoon levels of AVP used as a "cutoff" for a diagnosis of depression. See, Example 2.

Using this diagnostic criterion, this analysis demonstrated that afternoon AVP levels accurately predicted the status of 81% of the depressed patients and 76% of the control subjects (FIG. 2B). This indicates a false negative diagnosis error rate of 19% and a false positive diagnosis error rate of 24%.

EXAMPLE 3

Demonstration of Elevated TP in Clinically Depressed Subjects

The same study population of Example 1 was also evaluated for thymopoietin levels.

TP was extracted from the plasma samples collected from depressed and age/sex matched control subjects of Example 2 and assayed for TP content by the methods described in co-owned, concurrently filed, U.S. Patent Application entitled "Method of Measuring Thymopoietin Proteins in Plasma and Serum". Briefly, this method was performed as follows.

The samples of human plasma were acidified and allowed to incubate at room temperature for 1 hour to achieve dissociation and loaded onto an activated SepPak® C-18, reverse phase cartridge. To achieve dissociation, the sample had been acidified by dilution in 0.1% trifluoroacetic acid containing 0.01% Tween® 20 reagent to prevent non-specific absorption of free TP onto laboratory vessels and equipment. The SepPak® cartridge had been activated through the sequential passage of distilled, deionized water, 0.1% TFA:acetonitrile at a ratio of 20:80 and, finally, 0.1% TFA alone. The dissociated sample was passed through the SepPak® cartridges and the material passing through the cartridges was discarded. Each cartridge was then washed with 0.1% TFA containing 0.01% Tween® 20 reagent to completely remove all unbound material. Air was then passed through the cartridge to completely push all of the wash solution through the cartridge. The bound TP was eluted with the 20:80 ratio of 0.1% TFA:acetonitrile. The eluting solvent contained 0.01% Tween. Air was then passed through the cartridge to completely push all of the eluting solution through the cartridge. The eluting material was collected and saved. The acetonitrile in the collected material was evaporated, with warming, under a stream of nitrogen. The remaining aqueous phase was frozen and lyophilized to dryness.

The dried sample was then resuspended in 500 μL TP assay buffer and added at a volume of 200 μL/well to Immulon 4® polystyrene microtiter plates, that had been previously coated with rabbit anti-hTP 1-19 [amino acids 1-19 of SEQ ID NOS: 2, 4, 6] and post-coated with 1% BSA to prevent non-specific absorption. Synthetic hTP 1-52 [SEQ ID NO: 7] was added to wells at concentration ranging from 100 to 1.56 pg/mL at a volume of 200 μL/well to serve as a standard curve.

The samples/standards were incubated for 3 hours at 37 degrees C. The wells were then washed 3× with ELISA buffer and 200 μL biotinylated monoclonal antibody against hTP 29–50 [amino acids 29–50 of SEQ ID NOS: 2, 4, 6] added at an appropriate dilution in ELISA buffer containing 1% horse serum and incubated for 2 hours at 37 degrees C. The wells were then washed 3× with ELISA buffer. Streptavidin-polyhorseradish peroxidase was added at a dilution of 1:5000 (200 μL volume) and the incubation continued at room temperature for 30 minutes. The wells were then washed 5× with ELISA buffer and Ultra-Blue® substrate added for an additional 30 minutes incubation at room temperature. The optical density of each well was determined as a direct index of the amount of TP present.

Figure 3A:
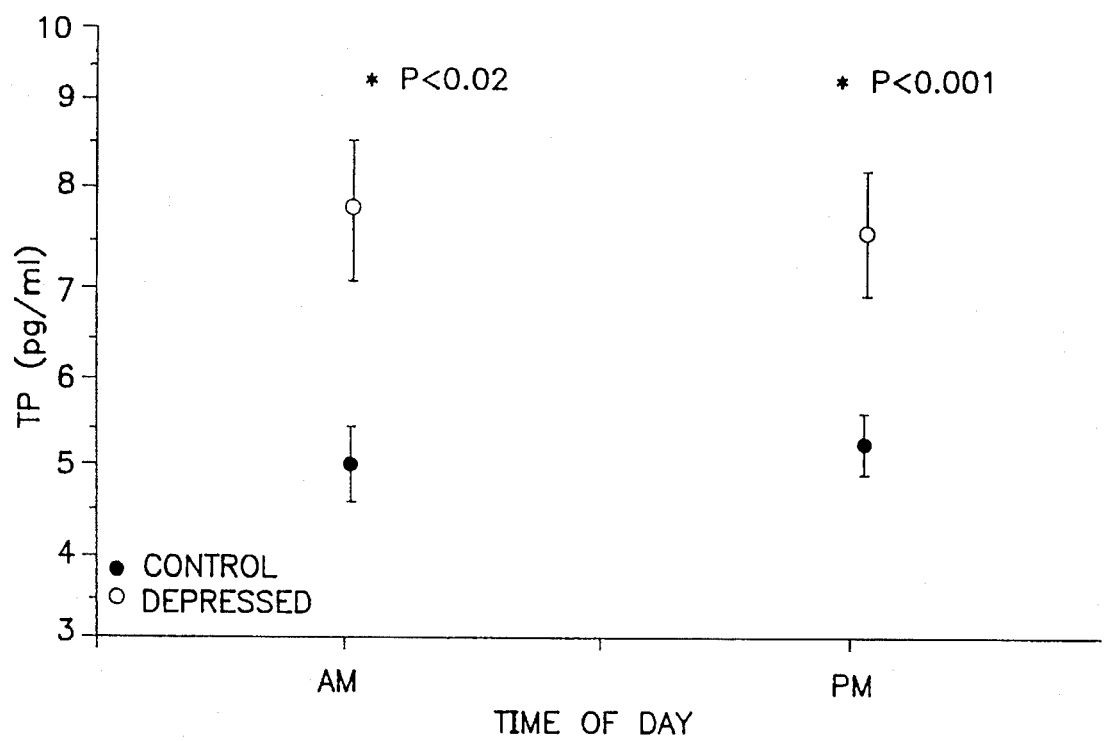
FIG. 3A is a graph plotting TP levels in pg/ml vs. time of day which illustrates the differences in mean (±SEM) TP levels between patients diagnosed as clinically depressed (open circle) and age/sex matched normal subjects (closed circle) at two different times of day. See Example 3.

Measurements were taken at the same time points as described above for AVP. FIG. 3A illustrates the TP levels (pg/ml) vs. time of day which illustrates the differences in mean (±SEM) TP levels between patients diagnosed as clinically depressed (open circle) and age/sex matched control subjects (closed circle) at two different times of day.

Measurable levels of TP were detected in all subjects; however, the levels of TP in the depressed subjects were significantly higher than those in control subjects at both the morning ($p<0.02$) and afternoon ($p>0.001$). In control subjects, the mean TP level was 5.3±1.5 pg/mL (mean±SD) and ranged from 2.5 to 7.9 pg/mL. In depressed patients, the mean TP level was 7.8±2.5 pg/mL (mean±SD) and ranged from 3.1 to 13.1 pg/mL.

A logistic regression model [Hosmer et al., cited above] was used to discriminate control and depressed individuals. The model determines the probability that an individual falls into either group. The logistical equation is solved to determine the level of TP which provides the greatest discrimination between the two groups. In the present example, this level was determined to be 6.4 pg TP/ml for afternoon TP values.

Using 6.4 pg/mL as the diagnostic criterion, individuals whose afternoon TP levels are greater than 6.4 pg TP/mL are classified as 'depressed' and those whose TP levels are less than 6.4 pg TP/mL are classified as 'normal'.

Figure 3B:
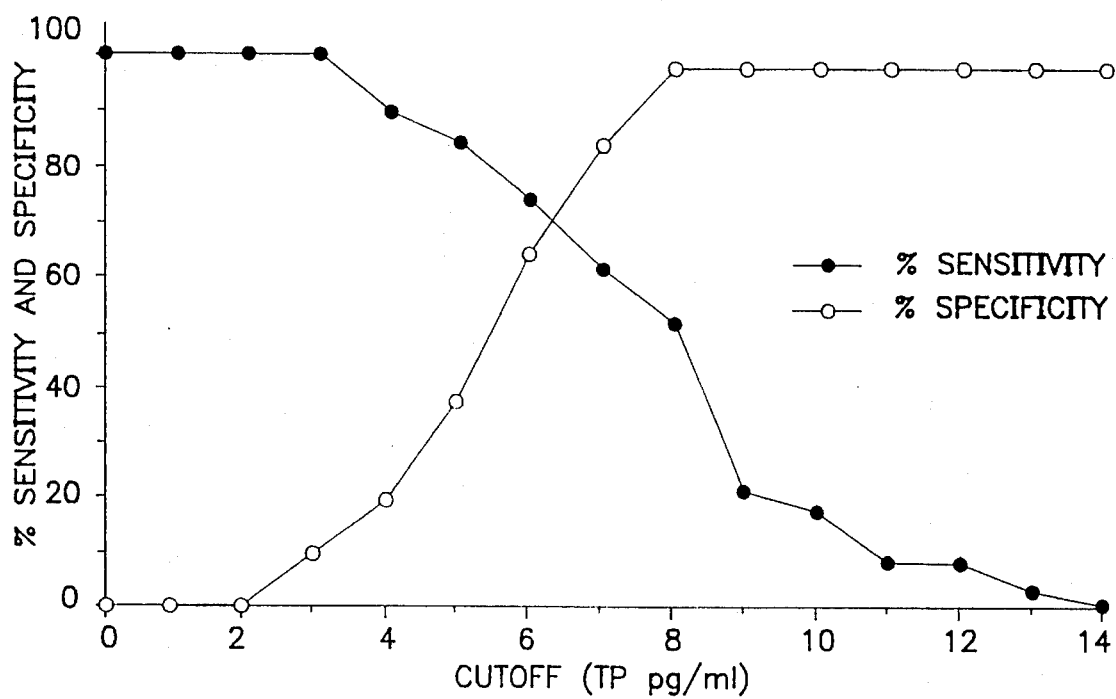
FIG. 3B is a graph plotting the sensitivity (false negative index) and the specificity (false positive index) for afternoon levels of TP used as a "cutoff" for a diagnosis of depression. See, Example 3.

With this diagnostic criterion, this analysis demonstrated that afternoon TP levels accurately predicted the status of 76% of the depressed patients and 81% of the control subjects (FIG. 3B). This indicates a false negative diagnosis error rate of 24% and a false positive diagnosis error rate of 19%.

EXAMPLE 4

Diagnostic Use of Combined TP and AVP Levels in Depressed Patients

The combined results of AVP and TP levels, measured as described in Examples 2 and 3, provide better discrimination than either AVP or TP levels alone. A stepwise logistic regression model was used to preliminarily assess whether both hormones together provide improved discrimination over either AVP or TP levels when considered separately. Results indicated significant improvement by using both AVP and TP.

Figure 4:
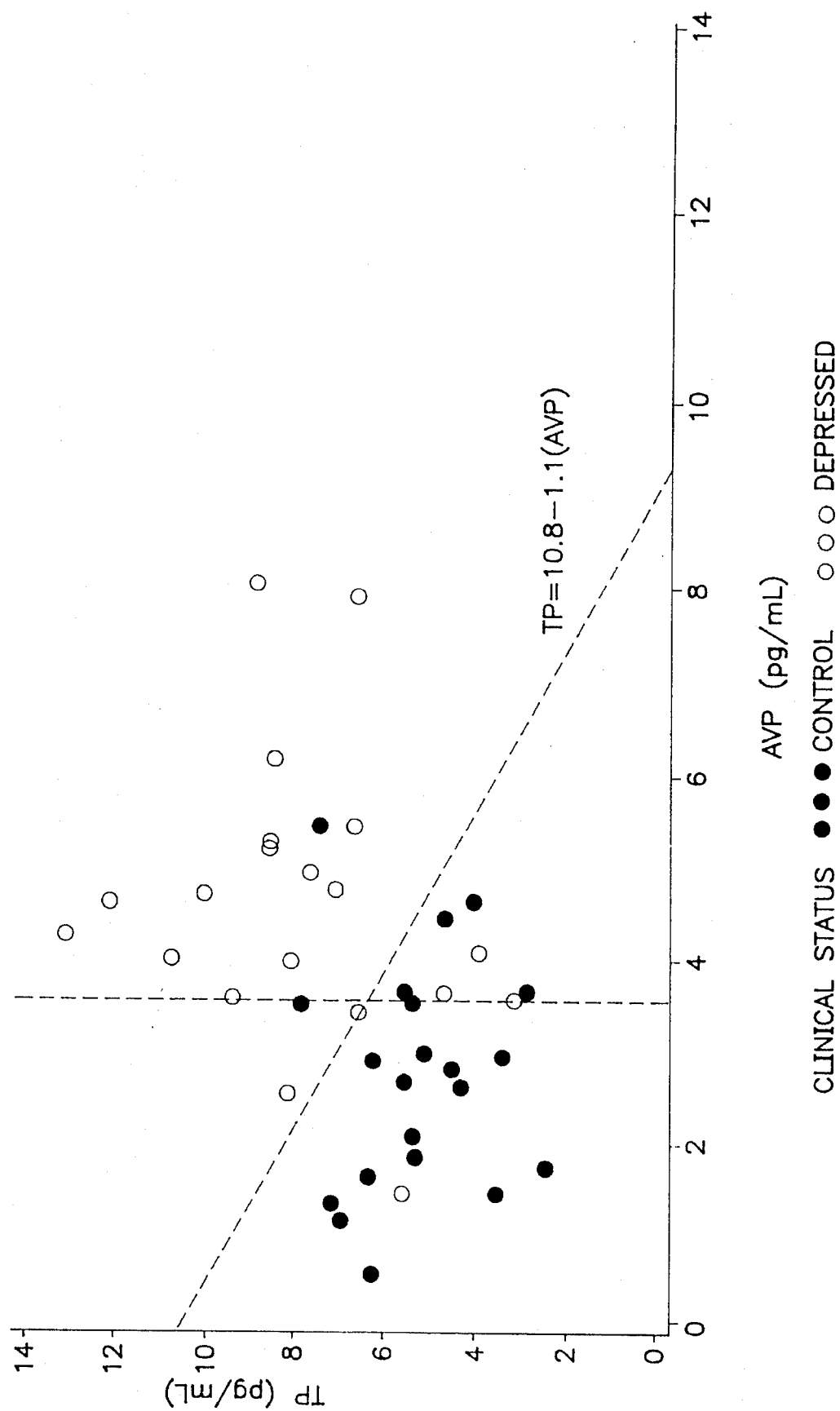
FIG. 4 is a graph plotting the diagnostic utility of "cutoff" levels of either 3.6 pg/ml for AVP alone (vertical line) or 6.4 pg/ml for TP alone (horizontal line). A straight line corresponding to TP=10.8 −1.1(AVP) (diagonal dashed line) is a linear discriminator used to predict clinical status as a function of the combined levels of TP and AVP. Subjects whose combined AVP and TP values are above the line are classified as depressed, while those whose values are below the line are designated normal. Control subjects are depicted by solid circles, depressed subjects are depicted by open circles. See, Example 4.

A logistic regression model [Hosmer et al, cited above] was then fit to these data, and the model parameters were used to differentiate depressed and normal individuals. Further substantiation was provided using a conditional logistic regression model, in which the age and sex matching were incorporated into the model. In addition, a linear discriminant analysis [see, D. Kleinbawm and L. Kupper, "Applied Regression Analysis and Other Multivariant Methods" Ducksbury Press, Ducksbury, Mass. (1978)] confirmed the results obtained by the logistic model. The solution to the linear discriminant analysis is a line which provides the maximum separation between depressed and control subjects. To illustrate this concept, FIG. 4 displays the TP and AVP levels in normal (solid circles) and depressed individuals (open circle). A dotted line (TP=10.8−(1.1×AVP)) is the linear discriminant function which best separates the data. Values above the line are classified as 'depressed' and values below the line are classified as 'normal'. Also indicated in FIG. 4 are the cutoff values for either hormone, when used separately. The AVP cutoff level is a vertical line (at 3.6 pg/mL), and the TP cutoff is a horizontal line (at 6.4 pg/mL).

FIG. 5 demonstrates the discriminating ability of afternoon measurements of AVP alone, TP alone, and AVP and TP in combination, as performed in this example, as predictors of depression. Clinical status is scored depressed (D) or normal (N). Classification rate is scored by the number of positives over the total tested and rated in percent sensitivity.

With this diagnostic criterion, the analysis demonstrated that combined afternoon AVP and TP levels accurately predicted the status of 81% of the depressed patients and 90% of the normal subjects (FIG. 4). This indicates a false negative diagnosis error rate of 19% and a false positive diagnosis error rate of 10% (FIG. 5).

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for aiding the diagnosis of depression in humans, comprising:
   providing a sample of serum or plasma from a first human subject suspected of having depression;
   providing a range of arginine vasopressin (AVP) levels previously obtained from normal control subjects;
   dissociating the AVP in the sample from its neurophysin carrier protein; and
   measuring the level of AVP in said first subject's sample by immunoassay,
   wherein detection of an AVP level in said first subject's sample which is statistically elevated over said normal control range is indicative of depression.

2. A method for aiding the diagnosis of depression in humans, comprising:
   providing a sample of serum or plasma from a first human subject suspected of having depression;
   providing a range of thymopoietin (TP) levels previously obtained from normal control subjects;
   dissociating the TP in the sample from its complexing protein; and
   measuring the level of TP in said first subject's sample in a immunoassay,
   wherein detection of a TP level in said first subject's sample which is statistically elevated over said normal control range is indicative of depression.

3. A method for aiding the diagnosis of depression in humans, comprising the steps of:
   (a) providing a sample of whole blood, serum or plasma from a first human subject suspected of having depression;
   (b) analyzing the arginine vasopressin (AVP) levels and thymopoietin (TP) levels previously obtained from normal and depressed control subjects in a two parameter logistic regression analysis to obtain a combined value which indicates the cutoff point between normal and depressed subjects;
   (c) dissociating the AVP from its neurophysin carrier protein and dissociating the TP in the sample from its complexing protein;
   (d) measuring the levels of AVP and TP in said first subject's sample in immunoassays;
   (e) combining the values of step (d); and
   (f) comparing the value of step (e) to said cutoff value, wherein a value of step (e) which is statistically elevated over said cutoff value indicates a diagnosis of depression.

4. The method according to claim 1 wherein said sample is obtained from said first subject in the afternoon.

5. The method according to claim 2 wherein said sample is obtained from said first subject in the afternoon.

6. The method according to claim 3 wherein said sample is obtained from said first subject in the afternoon.

7. A diagnostic kit useful as an aid in a diagnosis of depression comprising the anti-arginine vasopressin (AVP) antibodies and immunoassay components for the measurement of AVP levels in plasma or serum and anti-thymopoietin (TP) antibodies, reagents necessary to dissociate TP from its complexing protein, and the immunoassay components for the measurement of TP in plasma or serum.

8. The kit according to claim 7 further comprising reagents necessary to dissociate AVP from its neurophysin carrier protein.

* * * * *